United States Patent [19]

Hashimoto et al.

[11] Patent Number: 5,776,672
[45] Date of Patent: Jul. 7, 1998

[54] GENE DETECTION METHOD

[75] Inventors: Koji Hashimoto, Yokohama; Keiko Ito, Kawasaki; Yoshio Ishimori; Masanori Gotoh, both of Tokyo, all of Japan

[73] Assignee: Kabushiki Kaisha Toshiba, Kawasaki, Japan

[21] Appl. No.: 167,113

[22] Filed: Dec. 16, 1993

Related U.S. Application Data

[63] Continuation-in-part of Ser. No. 766,064, Sep. 27, 1991.

[30] Foreign Application Priority Data

Sep. 28, 1990 [JP] Japan .................................. 2-259011
Apr. 22, 1991 [JP] Japan .................................. 3-090879
Jul. 31, 1991 [JP] Japan .................................. 3-191868

[51] Int. Cl.$^6$ .............................. C12Q 1/68; C12Q 1/70
[52] U.S. Cl. ........................................... 435/6; 435/5
[58] Field of Search .............................. 435/5, 6, 808; 536/26.6; 935/77, 78

[56] References Cited

U.S. PATENT DOCUMENTS 5,001,051  3/1991  Miller et al. .............................. 435/6

FOREIGN PATENT DOCUMENTS 0 109 767  5/1984  European Pat. Off. .
0 135 159  3/1985  European Pat. Off. .
WO 86/04244  7/1986  WIPO .

OTHER PUBLICATIONS

Hashimoto et al, Supramol. Chem 2(4):265–270, 1993.

Ghosh et al., Nucleic Acid Res 15(13):5353–5372 (1987) "Covalent Attachment of Oligonucleotides to Solid Support".

*Primary Examiner*—Eggerton A. Campbell
*Attorney, Agent, or Firm*—Oblon, Spivak, McClelland, Maier & Neustadt, P.C.

[57] ABSTRACT

A single stranded nucleic acid probe having a base sequence complementary to the gene to be detected is immobilized onto the surface of an electrode or the tip of an optical fiber, and the nucleic probe is reacted with the gene sample denatured to a single stranded form, and then the nucleic acid probe hybridized with the gene is detected. In this procedure, to the reaction system consisting of the nucleic acid probe and the gene sample, a double stranded nucleic acid recognizing substance capable of binding specifically to the double stranded nucleic acid and being active electrochemically or optically is added. The detection of the nucleic acid probe is conducted by electrochemical or optical determination utilizing the electrode or optical fiber mentioned above. By this method, safer and more convenient detection of the gene is possible at a higher sensitivity even in a reduced time period.

9 Claims, 5 Drawing Sheets

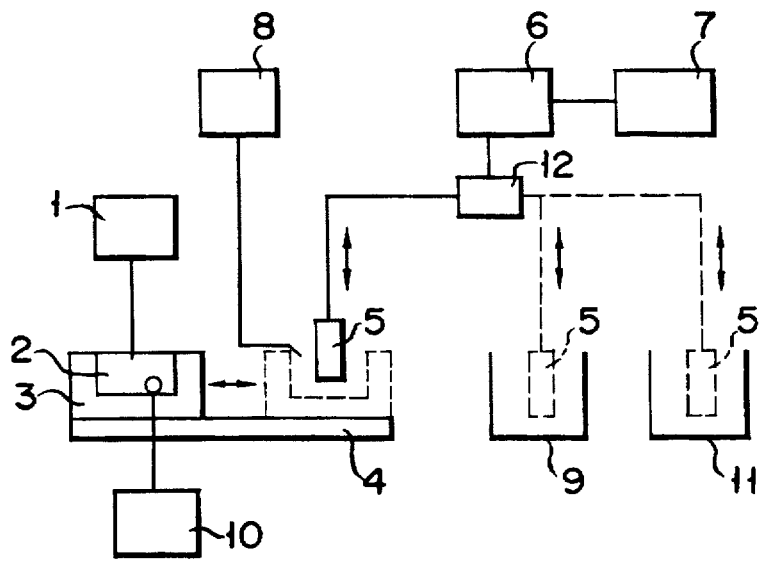
F I G. 1
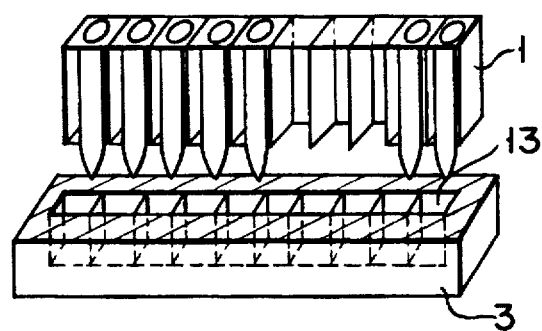
F I G. 2

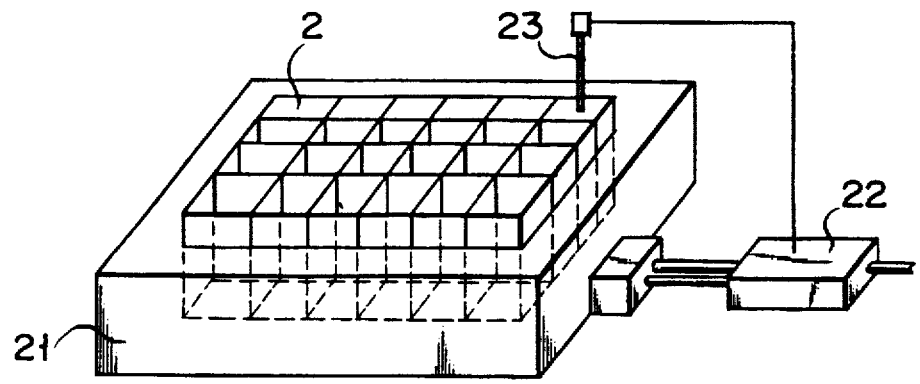
F I G. 3
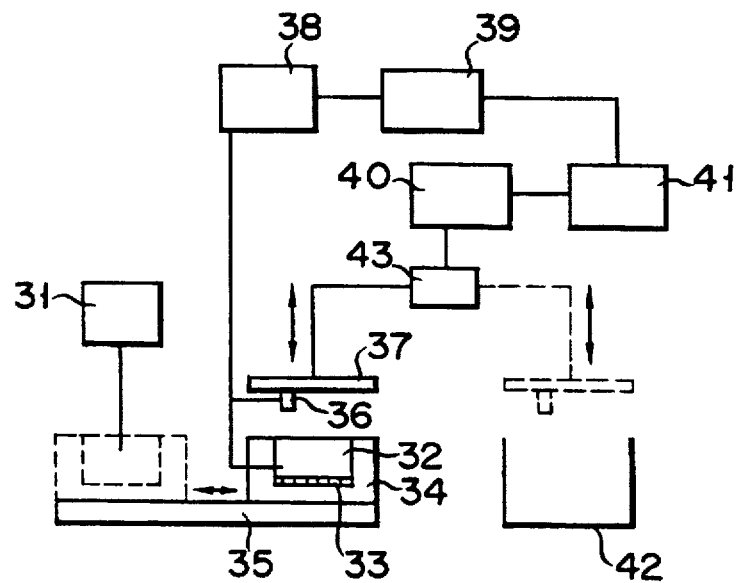
F I G. 4

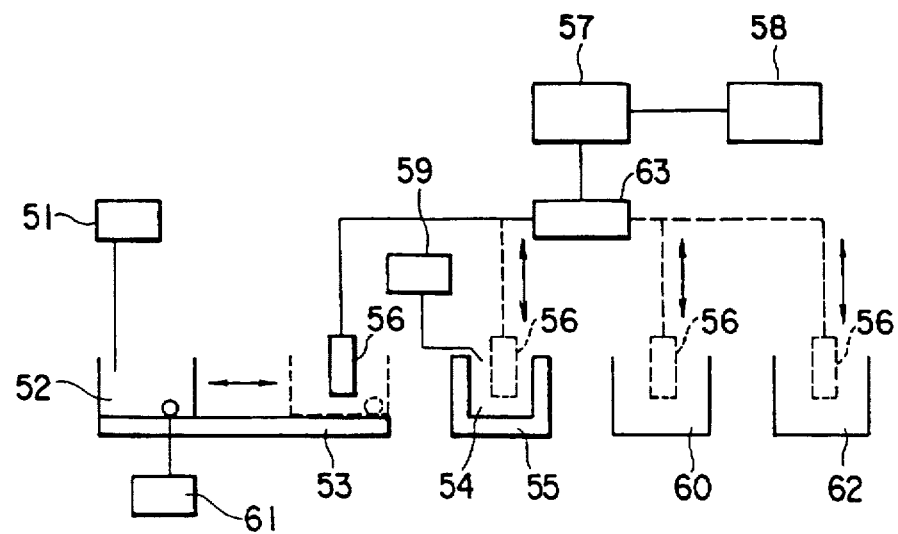
F I G. 7
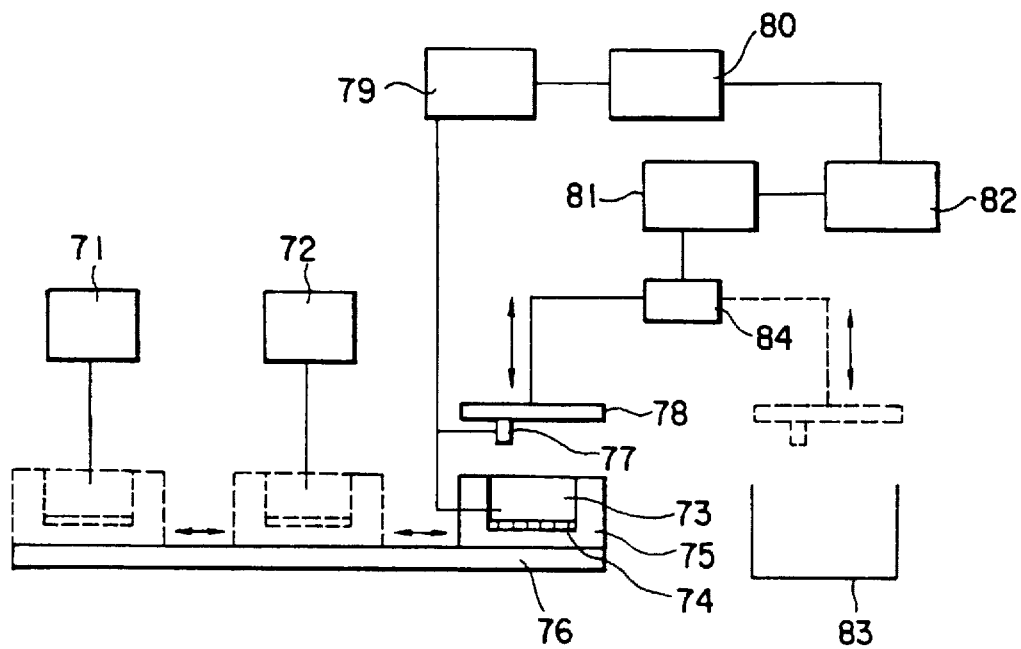
F I G. 8

POSITIVELY REACTED PROBE

A2 : CCCGCAC
A11 : CGCACAC
B4 : CACCGCG
B13 : GCGCATC
D2 : TCAGCCA
E9 : CCATCCG
F13 : CGCGCGA
G4 : GAGGGAA
G6 : AAACGAA
G15 : AACCCTC
H11 : TCTCAGA
I2 : GAGGCCA
I11 : CAAGCTA
J4 : TAAGGCC
J8 : CCTGAGC
J13 : GCAGGTG
K4 : AGGTGGT
L6 : GCACCGC
L13 : CACACCA
N7 : CGGCGCA
N10 : GGCGCAG
N13 : CATCTCA
O3 : ACCATCC

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:1:

GTACTTTACT GACAAACCCG ACCTAC                                                               26

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

CCGCAGCTGC ACTAATGATT GAACTTGAGA AG                                        32

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

TACTGGCCAC CTGTCCAGAG CATCAG                                                           26

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

GTGGTGGATT TGCCATCGGG TTTT                                                               24

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

CTTCACAGTC TCTACTGTGC                                                                                   20

( 2 ) INFORMATION FOR SEQ ID NO:6:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:6:

CGGATACCCA GTCTACGTGT                                                                                   20

( 2 ) INFORMATION FOR SEQ ID NO:7:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:7:

CCCTACAATC CCACCAGCTC AG                                                                                22

( 2 ) INFORMATION FOR SEQ ID NO:8:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:8:

CGGCAGTTCT GTGACAGGG                                                                                    19

( 2 ) INFORMATION FOR SEQ ID NO:9:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:9:

GAGCCGATAA CGCGTCCACT G                                                                                 21

( 2 ) INFORMATION FOR SEQ ID NO:10:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:10:

CACGCGCCCG CCCTACCTGA GGCCGCC                                                                           27

( 2 ) INFORMATION FOR SEQ ID NO:11:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:11:

TACTGGCCAC CTGTCCAGAG CATCAG     26

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:12:

GTGGGCGCCG GCGGTGTGGG     20

( 2 ) INFORMATION FOR SEQ ID NO:13:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:13:

ACCGCCGGCC AGGAGGAGTA     20

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:14:

GTTGGAGCTG GTGGCGTAGG     20

( 2 ) INFORMATION FOR SEQ ID NO:15:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:15:

ACAGCAGGTC AAGAGGAGTA     20

( 2 ) INFORMATION FOR SEQ ID NO:16:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:16:

GTTGGAGCAG GTGGTGTTGG    20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:17:

ACAGCTGGAC AAGAAGAGTA    20

( 2 ) INFORMATION FOR SEQ ID NO:18:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:18:

CCCGCACACC GCGCATCAGC CATCGCGCGA GGGAAACGAA CCCTCTCAGA GGCCAAGCTA    60

AGGCCTGAGC AGGTGGT    77

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:19:

TGCAGTTCCG GTGGCTGATC    20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:20:

TGCAGTTCCG GTGGCTGATC    20

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:21:

CGACTCGGAA GAAGAACAAG 20

GENE DETECTION METHOD

This application is a Continuation-In-Part of U.S. application Ser. No. 07/766,064, filed on Sep. 27, 1991; claiming foreign priority to Japanese Application 2-259011, filed on Sep. 28, 1990, claiming foreign priority to Japanese Application 3-90879, filed on Apr. 22, 1991, claiming foreign priority to Japanese Application 3-191868, filed on Jul. 31, 1991, claiming foreign priority to Japanese Application 91308770.6, filed on Sep. 26, 1991, claiming foreign priority to Japanese Application 4-242397, filed on Sep. 10, 1992.

BACKGROUND OF THE INVENTION

1. Field of the Invention

This invention relates to a novel gene detection method to detect a certain gene specifically and a device for such detection.

2. Description of the Related Art

A genetic information stored in DNA is expressed as a protein or an enzyme through mRNA. By the effects of such protein or enzyme, various compounds necessary to maintain the vital actions are biosynthesized and metabolized. Thus a life is present as a dynamic equilibrium system of various substances controlled by genes.

There are 50 to 100 thousands of human genes. When some of them involve abnormality or change, such as defect or duplication, the characteristics, types and amounts of the proteins synthesized are changed, resulting in the poorly balanced biosystem, which may cause diseases. Thus, by detecting known pathogenic genes, the diseases may be identified or prevented. Such diagnosis based on the genes themselves has been developed as a results of the recently advancing technology of gene engineering, and is called as gene diagnosis.

When compared with conventional diagnostic methods, the gene diagnosis has characteristics as mentioned below.

Considering the mechanisms of gene expression, it can be presumed that changes in genes occur prior to almost all biochemical changes. Therefore, gene diagnosis by means of detecting the genetic change enables the diagnosis or prognosis prior to development of a disease which is one of phenotypes. Accordingly, the dignosis and prognosis can be conducted before the development, in the latent period or at the earliest stage of the disease. This is the primary characteristic. As the secondary characteristic, gene diagnosis relating to the genetic diseases is independent from the organs or tissues to be analyzed since all genes in a living body are the same. This is particularly important in the diagnosis in fetus. Thus, this secondary characteristic enables the diagnosis simply by sampling amniotic fluid from a pregnant woman and analyzing the fetal cells suspending in the amniotic fluid.

Procedure of gene diagnosis conventionally employed is summarized as follows.

Genes are extracted from a samples and cleaved, if necessary, by appropriate restriction enzymes, and then subjected to electrophoresis and southern blotting.

Then a nucleic acid probe (usually radiolabelled) having the base sequence complementary to the gene to be detected is hybridized to the blotted gene. Subsequently, the hybridized nucleic acid probe is detected by exposing an X-ray film to the radiation emitted from the labeled probe at lower temperature to confirm the presence of the gene.

The conventional detection method mentioned above involves the limitation of the place of diagnosis due to the use of radioisotopes and should be conducted with sufficient care of handling reagents. For the purpose of reducing such inconvenience, safe labeling agents substituting the radioisotopes are being developed and several detection methods, in which probes are utilized, such as avidin-biotin bond method or enzymatic or fluorescent method and the like have already been suggested. However, these methods can not achieve the sensitivity superior to that of the method using radioisotopes. They also involve the problems of the time period required to detecting the gene as long as 2 or 3 days as well as complicated procedure of determination, on the other hand, quantification of a certain antigen or antibody present in a sample generally employs radioimmunoassay (RIA). However, RIA requires special instruments and authorized operators therefor capable of handling radioisotopes since this method also employs radioisotopes similarly as in the gene diagnosis methods mentioned above. In addition, waste disposal in this method should be done with particular care. As one of the other analytic methods, immunoelectrophoresis, which requires a long period for determination and has a poor sensitivity, can be suggested, although this method is not applicable in case of the samples containing only trace amount of test substance.

SUMMARY OF THE INVENTION

An objective of the present invention is to provide a method which is excellent in safety and convenience and is capable of detecting a certain gene at a high sensitivity in a reduced time period.

Accordingly, the gene detection method of the present invention is the method wherein a single stranded nucleic acid probe having a base sequence complementary to the gene to be detected is reacted with a gene sample denatured into a single stranded form and then the nucleic acid probe hybridized with the gene is detected to confirm the presence of the gene, characterized in that:

the nucleic acid probe is immobilized onto a carrier sensitive to a physical change;

a double stranded nucleic acid recognizing substance capable of binding specifically to a double stranded nucleic acid and being active physicochemically is added to the reaction system of the nucleic acid probe and the gene sample; and, the double stranded nucleic acid recognizing substance bound to the double stranded nucleic acid formed by conjugation of the nucleic acid probe and the gene to be detected is detected by means of physicochemical determination using the carrier, whereby detecting the presence of the nucleic acid probe hybridized with the gene to be detected.

Another object of the present invention is to provide a gene detection device which is excellent in safety and convenience and is capable of detecting a certain gene at a high sensitivity in a reduced time period.

Accordingly, the gene detection device of the present invention is the device comprising:

a gene detection sensor having a nucleic acid probe immobilized onto the surface of a carrier sensitive to a physical change;

a transportation means to transport the gene detection sensor;

a reaction bath to store a sample solution containing the gene sample denatured into a single stranded form, a double stranded nucleic acid being formed in said reaction bath on the gene sensor by hybridization of the gene sample and the nucleic acid probe immobilized on the surface of the gene sensor;

a temperature control means to control the temperature of the sample solution;

a washing means to remove unreacted gene sample by washing the gene sensor after hybridization of the nucleic acid probe with the gene sample; and a detection bath to store a double stranded nucleic acid recognizing substance, the double stranded nucleic acid recognizing substance being reacted with the double stranded nucleic acid formed on the surface of the gene sensor in said detection bath, whereby binding the double stranded nucleic acid recognizing substance with the double stranded nucleic acid in order to detect a physical change generated by the bound double stranded nucleic acid recognizing substance.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 shows a diagram schematically representing an example of the automatic gene detection device according to the present invention.

FIG. 2 shows a perspective view of another embodiment of the reaction bath and a gene sample purification device of the present automatic gene detection device shown in FIG. 1.

FIG. 3 shows a perspective view of an example of the temperature controller in the present automatic gene detection device shown in FIG. 1.

FIG. 4 shows a diagram schematically representing an example of the present automatic gene detection device utilizing electrochemiluminescene.

FIG. 7 shows a diagram schematically representing an example of the autonomic gene detection device utilizing carrier with a sample nucleic acid immobilized thereon.

FIG. 8 shows a diagram schematically representing an example of the autonomic gene detection device utilizing a carrier with nucleic acid sample immobilized thereon and electrochemiluminescence.

DETAILED DESCRIPTION OF THE PREFERRED EMBODIMENTS

Figure 5:
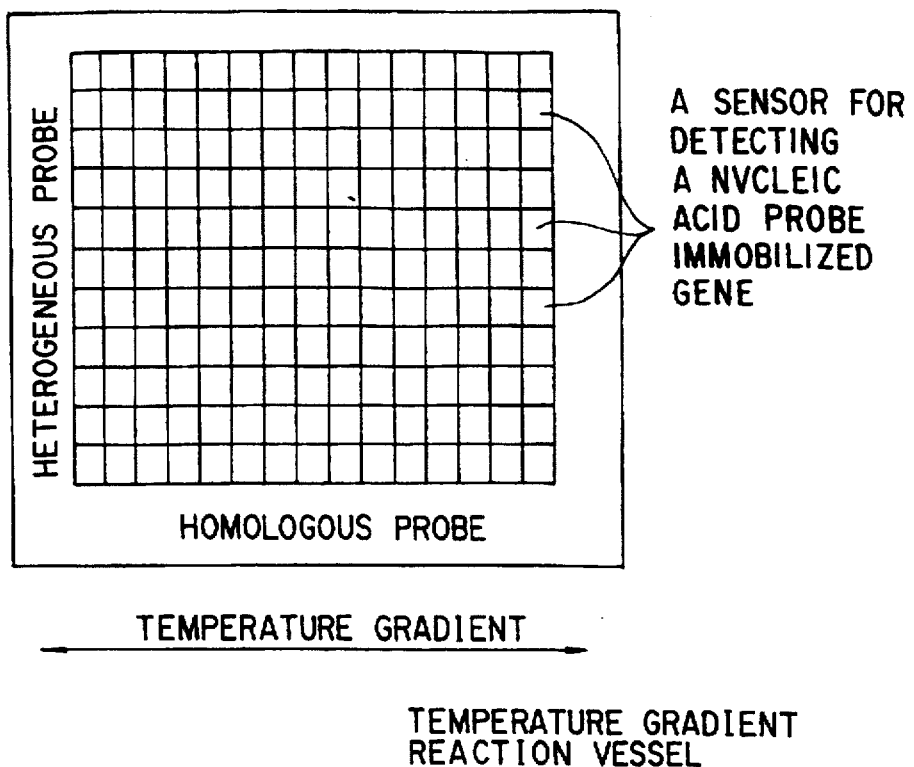
FIG. 5 shows a plan view of the temperature gradient reaction vessel used for screening a nucleic acid probe in Example 29.

In the present invention, the term "double stranded nucleic acid recognizing substance" means a substance which recognizes and binds specifically to a double stranded nucleic acid. Such substances are, for example, intercalating agents and biopolymers capable of recognizing double stranded nucleic acid.

The intercalating agents are characterized by their tendency to intercalate specifically to double stranded nucleic acid such as double stranded DNA. These intercalating agents have in their molecules a flat intercalating group such as phenyl group, which intercalates between the base pairs of the double stranded nucleic acid, whereby binding to the double stranded nucleic acid. Most of the intercalating agents are optically active and some of them are used in qualification of nucleic acids. Certain intercalating agents exhibit electrode response. Therefore, determination of physical change, especially optical or electrochemical change, may serve to detect the intercalating agents bound to a double stranded nucleic acid.

Electrochemically or optically active intercalating agents useful in the present invention are, but are not limited to, ethidium, ethidium bromide, acridine, aminoacridine, acridine orange, proflavin, ellipticine, actinomycin D, daunomycin, mitomycin C, HOECHST 33342, HOECHST 33258, aclarubicin, DAPI, Adriamycin, pirarubicin, actinomycin, tris (phenanthroline) zinc salt, tris (phenanthroline) ruthenium salt, tris (phenantroline) cobalt salt, di (phenanthroline) zinc salt, di (phenanthroline) ruthenium salt, di (phenanthroline) cobalt salt, bipyridine platinum salt, terpyridine platinum salt, phenanthroline platinum salt, tris (bipyridyl) zinc salt, tris (bipyridyl) ruthenium salt, tris (bipyridyl) cobalt salt, di (bipyridyl) zinc salt, di (bipyridyl) ruthenium salt, di (bipyridyl) cobalt salt, and the like. Other intercalating agents which are useful are those listed in Published Japanese Patent Application No. 62-282599.

In addition to the intercalating agents which are reversibly reacted themselves during oxidation-reduction reaction as listed above, the determination of electrochemical change using an electrode may employ a metal complex containing as a center metal a substance capable of undergoing electrically reversible oxidation-reduction reaction, namely, a metallo intercalater. Such metallo intercalaters include for example tris (phenanthroline) zinc salt, tris (phenanthroline) ruthenium salt, tris (phenanthroline) cobalt salt, di (phenthroline) zinc salt, di (phenanthroline) ruthenium salt, di (phenanthroline) cobalt salt, bipyridine cobalt salt, terpyridine platinum salt, phenanthroline platinum salt, tris (bipyridyl) zinc salt, tris (bipyridyl) ruthenium salt, tris (bipyridyl) cobalt salt, di (bipyridyl) zinc salt, di (bipyridyl) ruthenium salt, di (bipyridyl) cobalt salt and the like. Although the intercalating agents are not limited to those listed above, the complexes which or whose center metals have oxidation-reduction potentials not lower than or covered by that of nucleic acids are less preferable.

By using the intercalating agents capable of undergoing electrochemically reversible oxidation-reduction reaction, it is possible to determine the oxidation-reduction current repetitively. Accordingly, it is possible to conduct potential scanning several to several hundreds times and to sum up the values of the signals obtained, whereby enabling the amplification of the signals, resulting in a higher sensitivity of the detection.

When conducting the detection of the gene using an electrode, an intercalating agent exhibiting electrochemiluminescence may also be employed. Such intercalating agents are, but are not limited to, for example, luminol, lucigenin, pyrene, diphenylanthracene rubrene and acridinium derivaties. The electrochemiluminescene of the intercalating agents listed above may be enhanced by the enhancers such as luciferin derivatives such as firefly luciferin and dihydroluciferin, phenols such as phenyl phenol and chlorophenol as well as naphthols.

Optical signals generated by the electrochemiluminescence may directly be detected from the solution using, for example, photocounter. Alternatively, an optical fiber electrode produced by forming a transparent electrode at the tip of an optical fiber may also be used to detect the signal indirectly.

Since the electrode reaction or change in optical signal occur exclusively on the surface of the carrier, the detection can be conducted quite easily without removing unreacted probe or unreacted intercalating agent.

In the present invention, reaction of nucleic acid probe and the single stranded gene sample is generally conducted in a solution. Such reaction may be conducted in the presence of the intercalating agents listed above or the intercalating agents may be added after completion of the reaction.

As mentioned above, since most of the intercalating agents have themselves the optical activity or can exhibit the electrode response, direct determination is possible by means of optical or electrochemical procedure. When these intercalating agents are further bound with the substances which generate signals capable of being detected directly or indirectly, higher detection sensitivity can be obtained by determining the signals combined with the singles from the intercalating agents.

These substances which generate signals capable of being detected directly or indirectly include, for example, haptens such as biotin, trinitrobenzene sulfonic acid and dinitrobenzene sulfonic acid, fluorescent substances such as fluorescein isothiocyanate (FITC), phycocyanin and rhodamine, luminescent substances such as luminol, lucigenin and acridium ester derivatives as well as electrode active substances such as ferrocene and viologen. When using the substance, from which the signal can not directly being detected, such as the haptens listed above, enzyme-labelled anti-hapten antibodies such as enzyme-labelled avidin are used to determine the optical parameters such as absorbance, fluorescene, luminescene, quenching, circular dichroism and fluorescene polarization or, electrode activity is determined, whereby indirectly detecting the gene.

Although one molecule of these substances are usually bound to one molecule of a intercalating agent, several molecules of these substance may be bound to one molecule of the intercalating agent, whereby enhancing the sensitivity.

On the other hand, some biopolymers recognize and bind specifically to a double stranded nucleic acid. Accordingly, by labeling these biopolymers or the substances recognizing them with enzyme, fluorescent or luminescent substance and determining the electrochemical or optical change caused by the label to know the presence of the biopolymers, the detection of the double stranded nucleic acid may be possible.

Such biopolymers include, but are not limited to, DNA-binding proteins such as anti-DNA antibody, Croprotein, cI repressor, *E. coil* CRP (cAMP receptor protein) and lactose operon repressor and enzymes such as RNase H without catalyst activity. The biopolymers mentioned above may be derived from living bodies or may be synthesized.

Enzymes as labels to be bound to the biopolymers mentioned above are, but are not limited to, alkaline phosphatase, peroxidase, beta-galactosidase and glucose oxidase.

When detecting the electrochemical change using the biopolymers mentioned above, NADH in NAD+/NADH cycle and quinone in catechol/quinone cycle may be used. Thus, NADH or quinone formed by enzyme bound to a biopolymer may be oxidized or reduced by an electrode and the electrochemical change may be determined. Other substances involved in such electrochemical oxidation-reduction reaction may also be employed.

When detecting the optical change using the biopolymers mentioned above, an enzyme is bound to a biopolymer and a chemical luminescent substrate is used to conduct enzymatic reaction, or a fluorescent substance is bound to a biopolymer and the luminescene is directly detected. Chemical luminescent substrates useful in the present invention may be, but are not limited to, luminol, isoluminol, isoluminol derivatives and acridinium derivatives. When using the chemical luminescent substrates, enhancers can be used to enhance the chemical luminescence. Such enhancers may be, but are not limited to, luciferin derivatives such as firefly luciferin and dehydroluciferin, phenols such as phenyl phenol and chlorophenol as well as naphthols. Fluorescent substances useful in the present invention may be, but are not limited to, fluorescein, rhodamine and phycocyanin.

The amount of the double stranded nucleic acid recognizing substance to be added is not particularly specified, although the amounts sufficient to bind all double strands formed are preferable in view of the efficiency. When added in an excess amount, the double stranded nucleic acid recognizing substance remaining unreacted are washed off prior to the determination.

When the amount of the double stranded nucleic acid recognizing substance added is small and the concentration of it is low, only small amount of the unreacted recognizing substance remains in the system after the recognizing substance has bound to the double stranded nucleic acid formed. Thus, the double stranded nucleic acid recognizing substance is relatively concentrated on the carrier. In such state, the gene can be detected without washing off the sample DNA which has not reacted with the nucleic acid probe or free double stranded nucleic acid recognizing substance which has not bound to the double stranded nucleic acid formed, whereby enabling the continuous reactions from hybridization through detection of the gene intended in a single system. As mentioned above, the present invention is characterized in that the presence of a gene can be detected by determining a change in an electrochemical or a photochemical signal from a double-strand recognizing substance. Further, the progress of the reaction can be monitored by continuous observation of a change in the signal level resulting from the hybridization by means of a monitoring device. In conventional methods, the hybridization reaction is performed in a predetermined time which is supposed to be enough to complete the reaction based on empirical knowledge. Therefore, in some cases, an unnecessary period of time is given to the reaction; in other cases, on the contrary, the reaction has been terminated before hybridization is completed. However, direct or indirect monitoring of the signal generated from a double strand recognizing substance as a result of the hybridization reaction make it possible to determine the point by the time of which the hybridization reaction has proceed sufficiently to be detected, thereby conducting the hybridization reaction without failure and reducing the period of time for gene detection.

In the present invention, by varying the nucleic acid probe employed, various types of genes can be detected. Nucleic acid probes useful are such probes that have the base sequences complementary to entire or a part of base sequence of any of microorganisms contained in foods, plant viruses or viroids, pathogenic microorganisms or viruses infecting fishes, pathogenic microorganisms or viruses infecting human and causing infectious diseases, genes causing genetic diseases, activated proto-oncogenes and minisatellite sequence.

When using as a nucleic acid probe a probe having the base sequence complementary to entire or a part of the base sequence of a microorganism contained in a food, the microorganism contained in the food can directly be detected, thus enabling the food sanitary inspection. Such microorganisms contained in foods are, for example, pathogenic Escherichia coil, Staphylococcus as well as Salmonella.

When using as a nucleic acid probe a probe having the base sequence complementary to entire or a part of the base sequence of a plant virus or viroid, the plant virus or viroid with which plants are infected can be detected, thus enabling the infection diagnosis in agricultural fields. Examples of such plant viruses or viroids include tabacco mosaic virus and cauliflower mosaic virus.

When using as a nucleic acid probe a probe having the base sequence complementary to entire or a part of the base sequence of a pathogenic microorganism or virus infecting fishes, the pathogenic microorganism or virus with which fishes are infected can be detected, thus enabling the infection diagnosis in fishery field. Examples of such pathogenic microorganisms or viruses infecting fishes are pathogenic vibrio.

When using as a nucleic acid probe a probe having the base sequence complementary to entire or a part of the base sequence of a pathogenic microorganism or virus infecting human and causing infectious diseases, it is possible to conduct the infection diagnosis. Such pathogenic microorganisms infecting human and causing infectious diseases are, for example, pathogenic Streptococcus, Mycoplasma, Clostridium, Chlamydia, Salmonella, herpes simplex and cytomegalovirus.

When using as a nucleic acid probe a probe having the base sequence complementary to entire or a part of the base sequence of a gene causing a genetic disease, direct assay of the genetic disease is possible. Such genes causing genetic diseases are, for example, the genes causing adenosine deaminase deficiency and drepanocythemia.

When using as a nucleic acid probe a probe having the base sequence complementary to entire or a part of the base sequence of an activated proto-oncogene, it is possible to conduct the cancer diagnosis. Such activated proto-oncogenes are, for example, oncogenes listed in "Oncogene data book" (M. Shibuya, Pub. by Shujun-Sha).

When using as a nucleic acid probe a probe having the base sequence complementary to entire or a part of the base sequence of a minisatellite sequence, DNA finger print method useful for genetic studies, individual identification and parentage test can be conducted. Such minisatellite sequences are, for example, Myo sequence, Alu sequence, Per-6 sequence and Per sequence.

Although the length of a nucleic acid probe used in the present invention is not particularly specified and single stranded nucleic acids consisting of several to hundreds monomers may be employed, the lengths consisting of more than ten and less than a hundred monomers are preferable in order to increase S/N ratio and to obtain higher sensitivity in view of the fact describe below.

As already mentioned, a double stranded nucleic acid recognizing substance is such a substance that recognizes and binds specifically to a double stranded nucleic acid. However, the double stranded nucleic acid recognizing substance may bind to a single stranded nucleic acid in rare cases. Thus, it may bind to an unreacted nucleic acid probe immobilized on a carrier. When it binds in such a manner, S/N ratio is reduced, resulting in a poor detection accuracy. Accordingly, it is preferable to minimize the length of the nucleic acid probe as far as the detection of the intended gene is possible.

The detection of genes can also be done by labeling the nucleic acid probe in addition to using the double stranded nucleic acid recognizing substance mentioned above. In such cases, the labels to be used to label the nucleic acid probe may be any substance provided that it reacts directly or indirectly or causes some interaction with the double stranded nucleic acid recognizing substance and then a detectable signal is generated from either the double stranded nucleic acid recognizing substance or the label. In other word, an useful label gives a signal which is not generated when the nucleic acid is still present as a single strand and which is, once the probe reacts with the intended gene to form a double strand to which then the double stranded nucleic acid recognizing substance binds, then generated for the first time. The detection of gene is conducted by determining the signal generated by the reaction between the label and the double stranded nucleic acid recognizing substance. Such labels for the nucleic acid probe may be varied depending on the double stranded nucleic acid recognizing substance employed and may be, for example, fluorescent substances such as rhodamine and FITC, luminescent substances such as luminol and acridinium ester derivatives as well as enzymes and enzyme substrates. The double stranded nucleic acid recognizing substances may not be particularly specified and any of the substances listed above may be employed.

In the present invention, a nucleic acid probe is immobilized onto a carrier sensitive to a physical change as mentioned above. Although an electrode or optical fiber is preferably employed as the carrier for immobilizing the nucleic acid probe, other carrier such as photodiode, thermistor, ISFET, MOSFET, piezo elements, surface acoustic wave elements, quartz oscillator may also be employed.

The electrodes employed in the present invention may be, but are not limited to, carbon electrodes such as graphite, glassy carbon, pyrolytic graphite, carbon paste and carbon fiber, noble metal electrodes such as platinum, platinum black, gold, palladium and rhodium, oxide electrodes such as titanium oxide, tin oxide, manganese oxide and lead oxide, semiconductor electrodes such as Si, Ge, ZnO, CdS, $TiO_2$ and GaAs, as well as titanium. These electrodes may also be covered with conductive polymers to enhance the stability of the electrodes immobilized with probes. Monomolecular films may also be employed to cover the electrodes.

The nucleic acid probes may be immobilized onto the surfaces of the carriers such as electrodes and optical fibers by means of covalent bond, ionic bond and physical adsorption.

The examples of the procedure for the immobilization by means of covalent bond are the method in which the surface of the carrier is activated and then the nucleic acid probe is immobilized directly or indirectly through crosslinking agent and the method in which an active functional group is introduced into the nucleic acid probe to be immobilized onto the carrier followed by direct or indirect immobilization. The activation of the carrier surface may be conducted by electrolytic oxidation in the presence of oxidizing agent, or by air oxidation or reagent oxidation, as well as by covering with a film. Useful crosslinking agents may be, but are not limited to, silane couplers such as cyanogen bromide and gamma-aminopropyl triethoxy silane, carbodiimide and thionyl chloride and the like. Useful functional groups to be introduced to the nucleic acid probe may be, but are not limited to, amino group, carboxyl group, hydroxyl group, carbonyl group, phosphate group, aldehyde group and mercapto group. Other highly reactive functional groups may also be employed.

Once the surface of the carrier is oxidized for activation, an oxidized layer is formed on the surface. The nucleic acid probe binds to the substrate via this oxidized layer. By forming a thinner oxidized layer, S/N ration of detecting the gene is improved. The thickness of the oxidized layer is preferably not more than 500 A, more preferably not more than 100 A.

Introduction of the functional group into the terminal of the nucleic acid can be conducted by means of enzymatic reaction or by using DNA synthesizer. The enzymes useful in the enzymatic reaction may be, for example, terminal deoxynucleotidyl transferase, poly A polymerase, polynucleotide kinase, DNA polymerase, polynucleotide adenylyltransferase and RNA ligase. Polymerase chain reaction method (PCR method), nick translation method and random primer method may also be employed to introduce the functional group.

The functional group may be introduced to any part of the nucleic acid, such as 3' or 5' terminal, as well as a site randomly selected.

The nucleic acid probe with the functional group introduced may be immobilized as it is onto the carrier by immobilization reaction. However, the amino acid originally comprised in the nucleic acid may sometimes serve as a functional group instead of the functional group introduced, since the nucleic acid probe is a single strand. Thus the amino acid originally comprised in the nucleic acid is used for immobilization of the probe to the carrier, which affects the sensitivity.

The immobilization via the amino acid originally comprised in the nucleic acid probe may be prevented by, for example, the method as follows. First, the nucleic acid probe to which the functional group has been introduced is annealed with the DNA chain having the base sequence complementary to the probe to obtain a double strand. Then the functional group introduced is used to immobilize the double stranded nucleic acid to the carrier. Subsequently, thermal denaturation is conducted to form a single strand, whereby removing the DNA chain to which the functional group has not been introduced. The temperature during the thermal denaturation may usually be maintained from 90° to 98° C.

When the carrier to be used for immobilization of the nucleic acid probe is an electrode, the nucleic acid probe can be immobilized easily at a higher efficiency by utilizing physical adsorption. The physical adsorption of the nucleic acid probe onto the electrode surface can be conducted, for example, as follows. First, the electrode surface is washed with distilled water and alcohol using ultrasonic cleaner. Then the electrode is placed in the phosphate buffer (pH 7.0) containing the nucleic acid probe to adsorb the probe onto the surface of the substrate. In particular, the nucleic acid probe may be adsorbed to a carbon electrode in a high concentration and under a high temperature. During this procedure, potential of 0 to +1.0 V, preferably 0 to +0.1 V is applied to the electrode to accelerate the adsorption. Then the electrode having the nucleic acid adsorbed is placed in the solution containing nucleotides (ATP, CTP, GTP, TTP, dATP, dCTP, dGTP, dTTP and the like), and the electrode surface is coated with the nucleotides preferably while applying the potential of 0 to 1.0 V. By this treatment, non-specific adsorption of the sample nucleic acid or double stranded nucleic acid recognizing recognizing substance to the electrode surface can be prevented. Non-specific adsorption may also be prevented by using surfactants, fatty acids or fats.

Further, substances having effect on preventing non-specific adsorption may be, for example, amines such as sterylamine and aminononadecane, ammonium salts such as distearyldimethyl ammonium chloride.

When the nucleic acid probe is immobilized onto the carrier by adsorption, the adsorption of the nucleic acid probe can be facilitated by dissolving the nucleic acid probe in a solution having high ion strength, for example, ion strength of 0.1 or more.

Further the adsorption can be facilitated by adding a caotropic substance such as guanidinium salt, sodium iodide, potassium iodide, sodium (iso)thiocyanate, and urea.

The nucleic acid probe may also be immobilized to the carrier using a embedding agent used in the embedding method known as a procedure to immobilize the enzyme. The embedding agents useful in the present invention may be, but are not limited to, polyvinylchloride and polyacrylamide.

The nucleic acid probe may also be immobilized onto the electrode surface via a film. Such films may be, for example, conductive polymers such as polyacethylene, polypyrrole, polythiophene and polyaniline as well as polyethylene, polypropylene, poly (vinylchloride), poly (vinyl alcohol), poly (methylmethacrylate), poly (vinyl-idene fluoride), cellulose and lipid membrane. Monomolecular layer such as LB membrane and a multiple layer consisting of two or more monomolecular layers may also be employed.

Immobilization of the nucleic acid to the film or the membrane may be conducted in the manner similar to that used for the immobilization onto the surface of the carrier.

When the nucleic acid probe is immobilized to the film or the membrane by means of covalent bond, a functional group may be introduced to the film or the membrane instead of the nucleic acid probe. The functional groups suitable to be introduced into the film or the membrane may be same to those introduced into the nucleic acid probe. By introducing the functional group into the film or the membrane followed by reacting the nucleic acid probe to effect the immobilization, the probe can be immobilized at a higher density and more stably immobilized carrier with nucleic acid probe can be obtained when compared to the immobilization by introducing the functional group into the nucleic acid probe.

When the carrier to which the nucleic acid probe is immobilized via the film or the membrane is an electrode, the probe and the sample are hybridized as mentioned above while determining the membrane potentials before and after hybridization, whereby detecting the presence of the intended gene.

A carrier having the nucleic acid probe immobilized, when used as it is, tends to exhibit non-specific physical adsorption caused by a sample nucleic acid and a double stranded nucleic acid recognizing substance. Such non-specific adsorption may cause a reduced sensitivity. It can be suppressed by covering the carrier surface with the nucleic acid by means of physical adsorption or chemical bond after immobilization of the nucleic acid probe.

For this purpose, the nucleic acids to be used to cover the surface of the carrier are, for example, nucleo-sides such as adenosine, thymidine, guanosine and cytidine, nucleotides such as uridylic acid, cytidylic acid, adenylic acid and guanylic acid, synthetic oligonucleotide as well as naturally derived DNA such as salmon sperm DNA.

While the length and the base sequence of nucleic acid used to cover the surface of the carrier are not limited specifically as far as they do not cause the reaction with the nucleic acid probe immobilized on the surface of the carrier, a single stranded or double stranded nucleic acid of 1 to 100 bp is preferable.

Non-specific adsorption can also be suppressed by coating the carrier with the substances such as surfactants, fatty acids and fats. An example of such substance is stearylamine may be amines such as stearylamine, aminononadecane, and ammonium salts such as distearylaminedimethyl ammonium chloride.

In the gene detection method according to the present invention, the methods of immobilizing the nucleic acid probe to the carrier is not limited to those mentioned above and other method generally utilized to immobilizing biopolymers such as proteins to solid phases may widely be employed.

The amount of the nucleic acid probe to be immobilized to the carrier is not particularly limited, although a higher density of the nucleic acid probe immobilized results in a higher sensitivity of the detection, namely, a higher S/N ratio. The density of the nucleic acid probe immobilized is generally of the order of amol/cm$^2$ or higher.

The nucleic acid probe immobilized to a carrier especially to an electrode or optical fiber surface, can be quantified by determining an oxidation-reduction current or an optical signal of the nucleic acid or by determining an oxidation-reduction current or an optical signal of an electrochemically or optically active substance which binds specifically to the single stranded nucleic acid. Thus, when the carrier is an electrode, then the oxidation-reduction current from the nucleic acid or the intercalating agent is determined using a measurement system consisting of, for example, potentiostat, function generator, recorder and computer to quantify the nucleic acid immobilized. When the carrier is an optical fiber, then the optical signals from the nucleic acid or the intercalating agent bound to the nucleic acid, such as absorbance, fluorescence, luminescence, quenching, circular dichroism, fluorescence polarization or other optical parameters are determined using corresponding instruments to quantify the nucleic acid immobilized. By using these methods, it is possible to quantify the nucleic acid immobilized on the surface of the carrier more easily in a shorter period at a higher sensitivity when compared with the conventional methods which are quite complicated since the nucleic acid itself has no activity. The oxidation-reduction current from the nucleic acid may be the oxidation-reduction current from adenine, thymine, guanine or cytosine.

By imparting the function of an oscillator or rotator to the carrier immobilized with the nucleic acid probe, the flow near the surface of the carrier can relatively be increased, whereby facilitating the htbridization reaction and inhibiting the non-specific reaction, providing higher efficiency of the gene detection. The function of oscillator can be imparted to the carrier by utilizing mechanical oscillation, ultrasonic wave or electric or magnetic action.

As test samples, blood such as peripheral venous blood, leukocyte, serum, urine, feces, semen, saliva, cultured cell, tissue cells such as cells from various organs and other materials containing nucleic acids may be employed.

Although the extraction of nucleic acids from a test sample is conducted according to the conventional method, the double stranded nucleic acid recognizing substance mentioned above can be used for extraction and purification following the procedure described below.

First, the double stranded nucleic acid recognizing substance is immobilized to an appropriate support, which is then mixed with a test sample. The cells contained in the test sample is ruptured to release the nucleic acid, which is then bound to the double stranded nucleic acid recognizing substance. Subsequently, the support is separated from the test sample and the nucleic acid bound to the double stranded nucleic acid recognizing substance is separated from the support.

The supports useful herein may be, but are not limited to, polymer supports such as latex, polyethylene, polystyrene, and polypropylene, carbon materials such as activated carbon, metal particulates, ceramic materials, and magnetic materials such as magnetites, samarium-cobalt and ferrite. The forms of the supports are not particularly limited, but a particle whose size is within the range from 0.1 to 1000 µm, particularly from 1 to 100 µm, is preferable.

The cells contained in the test samples may be ruptured according to the standard method. For example, the support is agitated by means of the external force such as shaking or applying ultrasonic wave. Nucleic acid eluate may also be employed to release the nucleic acid from the cells. Such nucleic acid eluates are, for example, the solutions contianing surfactants such as SDS, Triton-X and Tween-20, and the solutions containing saponin, EDTA or proteases. When these solutions are used to release the nucleic acid, incubation at a temperature not lower than 37° C. may serve to facilitate the reaction.

After binding the nucleic acid to the double stranded nucleic acid recognizing substance immobilized to the support, the support is separated from the test sample by an appropriate means. The support which has been separated is first washed with a washing fluid (low salt concentration) to remove the unnecessary components, and then with a nucleic acid eluate (high salt concentration) to release the nucleic acid into the solution. When an intercalating agent is used as the double stranded nucleic acid recognizing agent, a non-polar organic solvent is used as the nucleic acid eluate.

When a magnetic particle is used to the support, agitation and separation of the support can conveniently be conducted by using external magnetic action which enables easier and rapid procedure.

When the content of the intended gene is quite small, the detection may also be conducted after amplification of the gene according to a known method. Representative gene amplification methods are methods utilizing enzymes, such as polymerase chain reaction (PCR) method. The enzymes useful in the gene amplification method may be, for example, DNA-dependent DNA polymerazes such as DNA polymerase and Taq polymerase, DNA-dependent RNA polymerazes such as RNA polymerase I, RNA-dependent RNA polymerazes such as Q beta replicase. Among methods using these enzymes, PCR method using Taq polymerase is a quite convenient method wherein the amplification can be repeated continuously only by controlling the temperature.

The samples thus obtained (course extract of nucleic acid, or purified solution of nucleic acid) are thermally denaturated at a temperature form 90° to 98° C., preferably not lower than 95° C. to prepare single strands. Then an electrode immobilized with nucleic acid probe or an optical fiber immobilized with nucleic acid probe is placed in the solution of the single stranded nucleic acid and hybridized at a temperature from 37° to 72° C. The optimum temperature for hybridization varies depending on the factors such as the base sequence and the length of the probe employed.

In such cases, the reaction rate is generally less satisfactory than in the case of the reaction in solution, since the hybridization reaction proceeds in a solid phase. However, this problem can be eliminated when using an electrode immobilized with the nucleic acid probe by applying a potential to the electrode surface before and/or during the hybridization raction to accelerate the reaction. The potential to be applied is preferably a positive potential, or a positive and negative potentials are alternatively applied. Such potential is applied continuously or intermittently as pulse. The potential applied may be a constant potential or a variable potential such as cyclic voltammetry, preferably a potential in the range of 0 to +2.0 V, more preferably a positive potential in the range of 0 to 1.0 V (sv. SCE).

Upon hybridization, unreacted nucleic acid may adsorb non-specifically to the electrode surface in addition to the intended gene bound to the nucleic acid probe. Such non-specific adsorption may reduce the S/N ratio of the gene detection. Usually the nucleic acid is negatively charged. Therefore the nucleic acid non-specifically adsorbed can be removed by applying the negative potential to the electrode. For this purpose, the potential to be applied is within the range from 0 to 2.0 V, preferably 0 to 1.5 V.

The double stranded nucleic acid recognizing substance may be added to the test sample either before or after the hybridization. Alternatively, a solution of the double stranded nucleic acid recognizing substance may previously be prepared, in which the electrode or optical fiber immobilized with the nucleic acid probe may be placed after hybridization. Since most of the double stranded nucleic acid recognizing substances are positively charged, non-specific adsorption of the recognizing substance to the carrier can be suppressed by applying positive potential in the cases where the carrier is an electrode.

Since the electrode reaction proceeds only near the surface of the electrode, a response of the intercalating agent bound to the double stranded nucleic acid to the electrode can be obtained exlcusively upon occurrence of hybridization. When using an electrode immobilized with a nucleic acid probe, a measurement system consisting of potentiostat, function generator and recorder may be used. Once the potential is set approximately to the oxidation-reduction potential of the intercalating agent, the potential is scanned. During the scanning, the oxidation-reduction current is determined to quantify the gene to be detected. This electrochemical determination may be done in a test solution or in other electrolyte solutions. It may also be done in hydrophilic or hydrophobic solvents.

When using an optical fiber immobilized with a nucleic acid probe, the gene to be detected is quantified by determining the optical parameters such as absorbance, luminescence, fluorescence, reflection, quenching, circular dichroism and fluorescence polarization.

The devices involving a nucleic acid probe immobilized to a carrier having a function of detecting signals, such as the electrode or optical fiber immobilized with the nucleic acid probe as mentioned above, are useful as gene detecting sensors. In order to use such devices as gene detecting sensors repeatedly, it is required to dissociate the sample which had been hybridized with the probe immobilized.

Dissociation of the sample from the probe may be conducted by treatments with heat, bases, acids, surfactants or ultrasonic wave. The heat treatment can be done by heating the double stranded nucleic acid formed at 98° C. for 5 minutes to denature the double stranded nucleic acid followed by rapid cooling. Alkaline treatment employs a buffer solution of pH 8.5 or higher or strong base solutions, while acid treatment employs a buffer solution of pH 4.5 or lower or strong acid solution. The surfactants used in the treatment with surfactants may be, but are not limited to, ionic or neutral surfactants such as SDS, Triton-X and Tween 20. For this purpose, the concentration of the surfactant is preferably 0.1% or higher. Ultrasonic treatment can be conducted by treating the sample for several seconds to several minutes with the ultrasonic wave having the frequency from 10 to 100 kHz.

The gene detection methods of the present invention are further described in the examples below.

EXAMPLE 1

Gene Detection Using Electrode Immobilized with Nucleic Acid Probe a. Immobilization of nucleic acid probe to Pt electrode surface Pt electrode was treated at a high temperature to air-oxidize the surface of the electrode. After activating the surface of the oxide layer by cyanogen bromide (CNBr), immobilization was conducted by immersing the electrode in the solution of thermally denatured single stranded nucleic acid probe (v-myc).

b. Gene detection using electrode immobilized with nucleic acid probe

As a test sample, pVM623 obtained by inserting v-myc fragment into pst I site of pUC 119 was employed. Linear pVM 623 was obtained by digesting with Hind III and then was subjected to the thermal denaturation at 98° C. The electrode immobilized with the nucleic acid probe was placed in the test sample, which is incubated for 15 minutes at 70° C. to anneal. During this procedure, acridine orange, an intercalating agent which has specificity to the double stranded DNA and is electrochemically active, was added.

After annealing, the electrode reaction was effected while determining the oxidation-reduction current produced to quantify v-myc contained in the test sample. As a result, v-myc could be detected in pg (picogram) order.

EXAMPLE 2

Gene Detection Using Optical Fiber Immobilized with Nucleic Acid Probe a. Immobilization of nucleic acid probe to optical fiber The tip of the optical fiber was treated with silane coupler (gamma-aminopropyl triethoxy silane: (gamma-APTES) and then the single stranded nucleic acid probe (v-myc) was immobilized using glutaraldehyde as a crosslinking agent.

b. Gene detection using optical fiber immobilized with nucleic acid probe

As a test sample, pVM 623 obtained by inserting v-myc fragment into Pst I site of pUC 119 was employed. Linear pVM 623 was obtained by digesting with Hind III and then was subjected to the thermal denaturation at 98° C. The optical fiber immobilized with the nucleic acid probe was placed in the test sample, which was incubated for 15 minutes at 70° C. to anneal. During this procedure, acridine which has specificity to the double stranded DNA was added.

After annealing, the fluorescent light emitted from acridine was determined to quantify v-myc contained in the test sample. As a result, v-myc could be detected in pg order.

EXAMPLE 3

Gene Detection Using Electrode Immobilized with Nucleic Acid Probe and Using Metallo Intercalator as an Intercalating Agent As a test sample, pVM 623 obtained by inserting v-myc fragment into Pst I site of pUC 119 was employed. Linear pVM 623 was obtained by digesting with Hind III and then was subjected to the thermal denaturation at 98° C. The electrode immobilized with the nucleic acid probe was placed in the test sample, which was incubated for 15 minutes at 70° C. to anneal. During this procedure, tris (1,10-phenanthroline) cobalt (III), an intercalating agent which has specificity to the double stranded DNA and is electrochemically active, was added.

After annealing, cyclic voltammetry was conducted and values of the oxidation-reduction current obtained by sweeping 30 times were summed up. As a result, v-myc could be detected in pg order.

EXAMPLE 4

Gene Detection Using Optical Fiber Electrode Immobilized with Nucleic Acid Probe and Utilizing Electrochemiluminescence As a test sample, pVM 623 obtained by inserting v-myc fragment into Pst I site of pUC 119 was employed. Linear pVM 623 was obtained by digesting with Hind III and then was subjected to the thermal denaturation at 98° C. The optical fiber electrode immobilized with the nucleic acid probe (v-myc) was placed in the test sample, which was incubated for 15 minutes at 70° C. to anneal. During this procedure, lucigen which has specificity to the double stranded DNA and is capable of generating electrochemically luminescence was added.

After annealing, electrochemical reaction was effected and the luminescence was detected through the optical fiber electrode immobilized with the nucleic acid probe. As a result, v-myc could be detected in pg order.

EXAMPLE 5

Gene Detection Using Electrode Immobilized with Nucleic Acid Probe and Using Anti-DNA Antibody as an Intercalating Agent a. Immobilization of nucleic acid probe to Pt electrode surface Pt electrode was treated at a high temperature to air-oxidize the surface of the electrode. After activating the surface of the oxide layer by cyanogen bromide (CNBr), immobilization was conducted by immersing the electrode in the solution containing thermally denatured single stranded nucleic acid probe (v-myc).

b. Gene detection using electrode immobilized with nucleic acid probe As a test sample, pVM 623 obtained by inserting v-myc fragment into Pst I site of pUC 119 was employed. Linear pVM 623 was obtained by digesting with Hind III and then was subjected to the thermal denaturation at 98° C. The electrode immobilized with the nucleic acid probe was placed in the test sample, which is incubated for 15 minutes at 70° C. to anneal. After washing the electrode, alkaline phosphatase-labeled anti-nucleic acid antibody which binds specifically to the double stranded nucleic acid was reacted, and washed again prior to adding NADP+ solution. Alkaline phosphatase hydrolyze NADP+ to generate NAD+.

NAD+ thus generated was determined by determining the current caused by oxidation of NADH in the system using alcohol dehydrogenase and diaphorase, whereby quantifying v-myc contained in the test sample. As a result, v-myc could be detected in pg order.

EXAMPLE 6

Gene Detection Using Optical Fiber Immobilized with Nucleic Acid Probe and Using Anti-DNA Antibody as an Intercalating Agent a. Immobilization of nucleic acid probe to optical fiber The tip of the optical fiber was treated with silane coupler (gamma-APTES) and then the single stranded nucleic acid probe (v-myc) was immobilized using glutaraldehyde as a crosslinking agent.

b. Gene detection using optical fiber immobilized with nucleic acid probe

As a test sample, pVM 623 obtained by inserting v-myc fragment into Pst I site of pUC 119 was employed. Linear pVM 623 was obtained by digesting with Hind III and then was subjected to the thermal denaturation at 98° C. The optical fiber immobilized with the nucleic acid probe was placed in the test sample, which was incubated for 15 minutes at 70° C. to anneal.

After annealing and washing, peroxidase-labelled anti-DNA antibody which binds specifically to the double stranded DNA was reacted. Then the sample was washed again, and reacted with $H_2O_2$ in an alkaline aqueous solution using luminol as a substrate and luciferin as an enhancer. The luminescence thus generated was determined to quantify v-myc contained in the test sample. As a result, v-myc could be detected in pg order.

REFERENCE EXAMPLE 1

Quantification of Nucleic Acid Probe on BPPG Electrode a. Introduction of amino group into nucleic acid probe A DNA labeling kit, Chemiprobe (ORGENICS Ltd.) was used to label carcinogenic gene v-myc (1.5 Kb), into which (6-aminohexyl) dATP was then introduced at 3' terminal using terminal deoxynucleotidyl transferase.

b. Immobilization of nucleic acid probe to electrode surface

As an electrode to which the nucleic acid is to be immobilized, basal plain pyrolytic graphite (BPPG) was employed. This electrode was subjected to electrolysis at 2.2 V in a solution containing 10% nitric acid and 2.5% potassium chromate to oxidize the surface. The electrode whose surface has been oxidized was then placed in a refluxed solution of 10% gamma-aminopropyl triethoxy silane in toluene at 120° C. for 30 minutes to effect silane treatment. After the electrode was washed with methanol, it was reacted in 1% glutaraldehyde solution for 30 minutes, and was washed again. The electrode was reacted in a solution containing 1 μg/ml v-myc having amino group introduced at a room temperature for 30 minutes, whereby producing an electrode immobilized with the nucleic acid probe.

c. Quantification of nucleic acid probe immobilized to electrode surface

Using the electrode immobilized with the nucleic acid probe thus obtained, cyclic voltammetry was conducted in 1/15M phosphate buffer solution (pH 7.0). As a result, oxidation current of 1 μA generated from adenine was measured by the electrode which had been subjected to 10 seconds oxidation, while oxidation current of 2 μA measured by the electrode which had been subjected to 60 seconds oxidation. From the determinatio using Chemiprobe kit, the amounts of nucleic acid immobilized to the surfaces of these electrodes were about 0.1 pmol/cm$^2$ and 0.2 pmol/cm$^2$, respectively. Such findings indicated that there may be correlation between the oxidation currents from the nucleic acids and the amounts of nucleic acid probe immobilized and that the nucleic acid probe immobilized may be quantified based on the electrode reaction of the nucleic acid.

REFERENCE EXAMPLE 2

Quantification of Nucleic Acid Probe on Optical Fiber a. Introduction of amino group into nucleic acid probe A DNA labeling kit called Chemiprobe was used to label carcinogenic gene v-myc (1.5 Kb), into which (6-aminohexyl) dATP was then introduced at 3' terminal using terminal deoxynucleotidyl transferase.

b. Immobilization of nucleic acid probe to optical fiber
The tip of the optical fiber was immersed in a solution of 10% gamma-aminopropyl triethoxy silane in toluene and refluxed at 120° C. for 30 minutes to effect silane treatment. The optical fiber was washed with methanol, it was reacted in 1% glutaraldehyde solution for 30 minutes and then washed again. The optical fiber was placed in a solution containing 1 μg/ml v-myc having amino group introduced and then reacted at a room temperature for 30 minutes, whereby producing an optical fiber immobilized with the nucleic acid probe.

c. Quantification of nucleic acid probe immobilized to optical fiber surface

Using the optical fiber immobilized with the nucleic acid probe thus obtained, the detection was attempted in 1/15M phosphate buffer solution (pH 7.0) containing 1.0 μM acridine orange and the fluorescence from acridine orange could be detected. The amount of the nucleic acid immobilized on the optical fiber surface was, when determined using Chemiprobe kit, was about 0.1 pmol/cm$^2$. These findings indicated that it is possible to determine the amount of the nucleic acid immobilized easily by determining the intensity of the fluorescence from the intercalating agent.

EXAMPLE 7

Acceleration of Hybridization of Nucleic Acid Sample with Nucleic Acid Probe Immobilized to Electrode As a test sample, pVM 623 obtained by inserting v-myc fragment into Pst I site of pUC 119 was employed. Linear pVM 623 was obtained by digesting with Hind III and then was subjected to the thermal denaturation at 98° C. Then the BPPG electrode immobilized with the nucleic acid probe was placed in the test sample, which was incubated for 15 minutes at 70° C. to effect annealing. During this procedure, 0.1 V (vs SCE) of potential was applied to the electrode.

Then acridine orange, which has specificity to the double stranded DNA and is electrochemically active, was added to effect the electrode reaction, during which the oxidation-reduction current generated was determined to quantify v-myc contained in the test sample. As a result, v-myc could be detected in pg order. The time required for hybridization which had conventionally been about 30 minutes was reduced to about 10 minutes.

EXAMPLE 8

Regeneration of Electrode Immobilized with Nucleic Acid Probe a. Immobilization of nucleic acid probe to Pt electrode surface Pt electrode was treated at a high temperature to air-oxidize the surface of the electrode. After activating the surface of the oxide layer by cyanogen bromide (CNBr), immobilization was conducted by immersing the electrode in the solution containing thermally denatured single stranded nucleic acid probe (v-myc).

b. Gene detection using electrode immobilized with nucleic acid probe

As a test sample, pVM 623 obtained by inserting v-myc fragment into Pst I site of pUC 119 was employed. Linear pVM 623 was obtained by digesting with Hind III and then was subjected to the thermal denaturation at 98° C. The electrode immobilized with the nucleic acid probe was placed in the test sample, which was incubated for 15 minutes at 70° C. to anneal. During this procedure, acridine orange, an intercalating agent which has specificity to the double stranded DNA and is electrochemically active, was added.

After annealing, the electrode reaction was effected while determining the oxidation-reduction current produced to quantify v-myc contained in the test sample. As a result, v-myc could be detected in pg order.

c. Regeneration of electrode immobilized with nucleic acid probe

By heating at 98° C. for five minutes the electrode immobilized with the nucleic acid probe which had once been used for determination, the sample pVM 623 was dissociated from the surface of the electrode immobilized with the nucleic acid probe. The electrode thus regenerated could be reused for the gene detection repeatedly at least 5 times thereafter.

EXAMPLE 9

Regeneration of Optical Fiber Immobilized with Nucleic Acid Probe a. Immobilization of nucleic acid probe to optical fiber The tip of the optical fiber was treated with silane coupler (gamma-APTES) and then the single stranded nucleic acid probe (v-myc) was immobilized using glutaraldehyde as a crosslinking agent.

b. Gene detection using optical fiber immobilized with nucleic acid probe

As a test sample, pVM 623 obtained by inserting v-myc fragment into Pst I site of pUC 119 was employed. Linear pVM 623 was obtained by digesting with Hind III and then was subjected to the thermal denaturation at 98° C. The optical fiber immobilized with the nucleic acid probe was placed in the test sample, which was incubated for 15 minutes at 70° C. to anneal. During this procedure, acridine which has specificity to the double stranded DNA was added.

After annealing, the fluorescent from acridine was determined to quantify v-myc contained in the test sample. As a result, v-myc could be detected in pg order.

c. Regeneration of optical fiber immobilized with nucleic acid probe

By heating at 98° C. for five minutes the optical fiber immobilized with the nucleic acid probe which had once been used for determination, the sample vPM 623 was dissociated from the surface of the optical fiber immobilized with the nucleic acid probe. The optical fiber thus regenerated could be reused for the gene detection repeatedly at least 5 times thereafter.

EXAMPLE 10

Gene Detection Using Intercalating Agent to which Substance Generating Signals which can be Detected Directly or Indirectly is Bound.

a. Preparation of electrode immobilized with nucleic acid probe (6-aminohexyl) dATP was introduced at 3' terminal into synthetic oligonucleotide probe (20 mer) against to a carcinogenic gene v-myc using terminal deoxynucleotidyl transferase.

On the other hand, a basal plain pyrolytic graphite (BPPG) electrode was subjected to electrolysis at 2.2 V in a solution containing 10% nitric acid and 2.5% potassium chromate to oxidize the surface of BPPG electrode. The electrode was then placed in a refluxed solution of 10% gamma-APTES in aniline at 120° C. for 30 minutes to effect silane treatment. After the electrode was washed with methanol, it was reacted in 1% glutaraldehyde solution for 30 minutes and washed again.

This BPPG electrode was reacted in a solution containing 1 μg/ml synthetic oligonucleotide probe, which has specificity to v-myc, having amino group introduced at a room temperature for 30 minutes, whereby producing an electrode immobilized with the nucleic acid probe.

b. Gene detection using electrode immobilized with nucleic acid probe

As a test sample, pVM 623 obtained by inserting v-myc fragment into Pst I site of pUC 119 was employed. Linear pVM 623 was obtained by digesting with Hind III and then was subjected to the thermal denaturation at 98° C. BPPG electrode immoblized with the nucleic acid probe was place in the test sample, which was incubated at 70° C. to anneal. Subsequently, acridine orange bound to ferrocene was added in such an amount that final concentration of 1 μM was obtained. After washing, it was subjected directly to the electrode reaction, during which the oxidation-reduction current was determined to quantify v-myc contained in the sample.

When the sample did not contained the gene intended, then the oxidation-reduction current from ferrocene was not detected. However, in the case of the sample containing the gene intended, the oxidation-reduction current could be detected, and ultimately v-myc can be detected in the order of pg. Since no B/F separation was required, the detection was completed within 30 minutes.

EXAMPLE 11

Gene Detection Using Intercalating Agent to which Substance Generating Signals which can be Detected Directly or Indirectly is Bound First, the electrode immobilized with the nucleic acid probe was prepared in the manner similar as in Example 10, and then it was immersed in a solution of nucleotides (dATP, dCTP, dGTP and dTTP) for the purpose of preventing non-specific adsorption of sample DNA.

As a test sample, pVM 623 obtained by inserting v-myc fragment into Pst I site of pUC 119 was employed. Linear pVM 623 was obtained by digesting with Hind III and then was subjected to the thermal denaturation at 98° C. Then BPPG electrode immobilized with the nucleic acid probe was placed in the test sample, which was incubated at 70° C. to anneal. During this procedure, 0.1 V (vs SCE) of potential was applied to the electrode.

After reaction, an intercalating agent which has specificity to the double stranded DNA and is electrochemically active, namely tris (phenanthroline) cobalt salt was added. After tris (phenanthroline) cobalt salt was bound to the double stranded nucleic acid, negative charge was applied to the electrode to remove the substances binding non-specifically. Subsequently, the oxidation-reduction current of the intercalating agent was determined to quantify v-myc contained in the test sample. As a result, v-myc could be detected in pg order.

EXAMPLE 12

Gene Detection Using Optical Fiber Immobilized with Nucleic Acid Probe Labeled with Luminol a. Preparation of optical fiber immobilized with nucleic acid probe labeled with luminol (6-aminohexyl) dATP was introduced at 3' terminal into synthetic oligonucleotide probe (20 mer) against to a carcinogenic gene v-myc using terminal deoxynucleotidyl transferase. This nucleic acid probe was labeled with luminol and then immobilized to the surface of the optical fiber by means of physical adsorption.

b. Gene detection using optical fiber immobilized with nucleic acid probe

As a test sample, pVM 623 obtained by inserting v-myc fragment into Pst I site of pUC 119 was employed. Linear pVM 623 was obtained by digesting with Hind III and then was subjected to the thermal denaturation at 98° C. The optical fiber immobilized with the nucleic acid probe labeled with luminol was placed in the test sample, which was incubated at 55° C. to anneal. During this procedure, ethidium bromide which binds specifically to the double stranded nucleic acid was added. The ethidium bromide is concentrated on the surface of the optical fiber. Subsequently, luciferin and $H_2O_2$ was used to generate the luminescence from luminol, whereby exciting ethidium bromide. Fluorescence generated from the excited ethidium bromide was determined to quantify v-myc contained in the test sample. As a result, v-myc could be detected in the order of pg.

EXAMPLE 13

Gene Detection Using Optical Fiber Immobilized with Nucleic Acid Probe Labeled with O-phenylenediamine a. Preparation of optical fiber immobilized with nucleic acid probe labeled with O-phenylenediamine (6-aminohexyl) dATP was introduced at 3' terminal into synthetic oligonucleotide probe (20 mer) against to a carcinogenic gene v-myc using terminal deoxynucleotidyl transferase. This nucleic acid probe was labeled with O-phenylenediamine and then immobilized to the surface of the optical fiber by means of physical adsorption.

b. Gene detection using optical fiber immobilized with nucleic acid probe

As a test sample. pVM 623 obtained by inserting v-myc fragment into Pst I site of pUC 119 was employed. Linear pVM 623 was obtained by digesting with Hind III and then was subjected to the thermal denaturation at 98° C. The optical fiber immobilized with the nucleic acid probe labeled with O-phenylenediamine was placed in the test sample, which was then incubated at 55° C. to anneal. After annealing. anti-double stranded DNA antibody labeled with alkaline phosphatase was added. In this method, the antibody was concentrated on the surface of the optical fiber when intended gene was present in the sample, whereby undergoing the enzymatic reaction. resulting in the absorbance at 405 nm. The absorbance at 405 nm was determined to quantify v-myc contained in the test sample. As a result, v-myc could be detected in the order of pg.

REFERENCE EXAMPLE 3

Immobilization to Electrode Surface Via Amino Group Introduced into Nucleic Acid Probe a. Preparation of nucleic acid probe into which amino group is introduced 2 primers (20 mer) used for amplification of about 1.0 Kb fragment of carcinogenic gene v-myc were synthesized using DNA synthesizer (Applied biosystem, PCR-MATE EP). An amino group was further introduced to one of the primer at 5' terminal using Aminolink 2 (Applied biosystem).

These two synthetic primers were admixed each in the concentration of 100 µg/ml and subjected to the treatment at 95° C. for 5 minutes followed by 37° C. for 30 minutes to anneal to obtain a double stranded nucleic acid probe.

b. Immobilization of nucleic acid probe to electrode surface

As an electrode to which the nucleic acid is to be immobilized, basal plain pyrolytic graphite (BPPG) was employed. This electrode was subjected to electrolysis at 2.2 V in a solution containing 10% nitric acid and 2.5% potassium chromate to oxidize the surface. The electrode whose surface had been oxidized was then placed in a refluxed solution of 10% gamma-APTES in aniline at 120° C. for 30 minutes to effect silane treatment. After the silane treated electrode was washed with methanol, it was reacted in 1% glutaraldehyde solution for 30 minutes, and then washed again.

This BPPG electrode was reacted in a solution containing 100 µg/ml of double stranded nucleic acid probe prepared in step a at a room temperature for 30 minutes, whereby immobilizing the double stranded nucleic acid on the surface of the electrode. Then the electrode was further subjected to thermal denaturation at 95° C. for 5 minutes to remove the DNA chain without the functional group introduced, whereby producing an electrode immobilized with the nucleic acid probe.

EXAMPLE 14

Gene Detection Using Electrode Immobilized with Nucleic Acid Probe Via Lipid Membrance a. Preparation of electrode immobilized with nucleicacid probe Lipid membrane was formed using phosphatidylethanolamine on the surface of basal plain pyrolytic graphite (BPPG) electrode. On the other hand, (6-aminohexyl) dATP was introduced at 3' terminal into carcinogenic gene v-myc (1.5 Kb) using terminal deoxynucleotidyl transferase.

After treating lipid membrane-modified BPPG electrode with glutaraldehyde, it was reacted in 1 µg/ml solution of v-myc to which amino group had been introduced for 30 minutes at a room temperature, whereby producing an electrode immobilized with the nucleic acid probe.

b. Gene detection using electrode immobilized with nucleic acid probe

As a test sample, plasmid pVM 623 obtained by inserting v-myc (1.5 Kb) into Pst I site of pUC 119 was employed.

The test sample was thermally denatured at 95° C. and then the electrode immobilized with the nucleic acid prepared in step a was placed in the sample to effect hybridization at 55° C. Determination of the membrane potential of the electrode immobilized with the nucleic acid was started before the initiation of hybridization. The membrane potential changed as the hybridization proceeded, and plateaued about 2 hours after initiation of reaction. Thus, when using the electrode immobilized with the nucleic acid probe via the membrane, the gene can be detected while monitoring the hybridization reaction. As a result, the intended gene could be detected in the order of pg.

EXAMPLE 15

Gene Detection Using Electrode Immobilized with Nucleic Acid Probe and Blocked by Synthetic Oligonucleotide a. Preparation of electrode immobilized with nucleic acid probe (6-aminohexyl) dATP was introduced at 3' terminal into synthetic oligonucleotide probe (20 mer) against to a carcinogenic gene v-myc using terminal deoxynuclotidyl transferase.

On the other hand, BPPG electrode was subjected to electrolysis at 2.2 V in a solution containing 10% nitric acid and 2.5% potassium chromate to oxidize the surface of the electrode. The electrode whose surface had been oxidized was then placed in a refluxed solution of 10% gamma-APTES in aniline at 120° C. for 30 minutes to effect silane treatment. After the silane-treated electrode was washed with methanol, it was reacted in 1% glutaraldehyde solution for 30 minutes, and then washed again.

This electrode was reacted in a solution containing 1 µg/ml of the probe to which amino group had been introduced at a room temperature for 30 minutes, whereby producing an electrode immobilized with the nucleic acid probe.

This electrode was immersed in a solution of synthetic nucleotide (20 mer) to adsorb the synthetic nucleotide on the surface of electrode.

b. Gene detection using electrode immobilized with nucleic acid probe

As a test sample, pVM 623 obtained by inserting v-myc fragment into Pst I site of pUC 119 was employed. Linear pVM 623 was obtained by digesting with Hind III and then was subjected to the thermal denaturation at 98° C. The BPPG electrode immobilized with the nucleic acid probe produced in step a above was placed in the test sample, which was then incubated at 70° C. to anneal. Subsequently, an intercalating agent acridine orange which binds specifically to the double stranded nucleic acid and has electrode activity was added and then the electrode reaction was conducted, during which the oxidation-reduction current generated was determined to quantify v-myc contained in the test sample.

As a result, v-myc could be detected in the order of pg. S/N ratio observed was higher than that of the electrode whose surface was not blocked.

EXAMPLE 16

Amplification and Detection of Intended Gene a. Amplification of intended gene

As a test sample, pVM 623 (4.6 Kb) obtained by inserting v-myc fragment into Pst I site of pUC 119 was employed. Linear pVM 623 was obtained by digesting with Hind III and then the concentration was adjusted to 1 femtomol (10-15 mol). The sample was subjected to PCR using the condition shown below as one cycle and repeating the cycle 30 times to amplify 1 Kb fragment of v-myc.

Denaturation: 94° C. for 1 minute
Primer annealing: 55° C. for 1 minute
DNA elongation: 72° C. for 1 minute b. Gene detection using electrode immobilized with nucleic acid probe The sample amplified by PCR was thermally denatured at 98° C. and BPPG electrode immobilized with nucleic acid probe was placed in the sample, which was then incubated at 70° C. for 15 minutes to effect annealing. During this procedure, acridine orange, an intercalating agent which has specificity to the double stranded nucleic acid and has the electrode activity, was added to the sample. Subsequently, the electrode reaction was conducted while determining the oxidationreduction current generated to quantify v-myc contained in the sample. As a result, the presence of v-myc could be confirmed.

REFERENCE EXAMPLE 4

Amplification and Detection of Intended Gene a. Amplification of intended gene

As a test sample, pVM 623 (4.6 Kb) obtained by inserting v-myc fragment into Pst I site of pUC 119 was employed. Linear pVM 623 was obtained by digesting with Hind III and then the concentration was adjusted to 1 femtomol ($10^{-15}$ mol). The sample was subjected to PCR using the condition shown below as one cycle and repeating the cycle 30 times to amplify 1 Kb segment of v-myc.

Denaturation: 94° C. for 1 minute
Primer annealing: 55° C. for 1 minute
DNA elongation: 72° C. for 1 minute The primer was previously labeled with biotin prior to use.

b. Gene detection using optical fiber immobilized with nucleic acid probe

The sample obtained by PCR was thermally denatured at 98° C. and the optical fiber immobilized with nucleic acid probe was placed in the sample, which was then incubated at 70° C. for 15 minutes to effect annealing. Subsequently, avidin-labelled horse radish peroxidase was reacted and the fiber was washed. After adding luminescence substrate luminol, $H_2O_2$ and enhancer, the luminescence was detected via the optical fiber. As a result, the presence of v-myc was confirmed.

EXAMPLE 17

Gene Detection while Inhibiting Non-Specific Adsorption of Nucleic Acid to Electrode Immobilized with Nucleic Acid Probe As a test sample, pVM 623 obtained by inserting v-myc fragment into Pst I site of pUC 119 was employed. Linear pVM 623 was obtained by digesting with Hind III and then was subjected to the thermal denaturation at 98° C. The BPPG electrode immobilized with the nucleic acid probe was placed in the test sample, which was incubated at 70° C. to effect annealing. After annealing, -1.5 V (vs SCE) potential was applied to the electrode to remove DNA adsorbing the electrode surface non-specifically and physically.

Then acridine orange, an intercalating agent which has specificity to the double stranded DNA and has electrode activity, was added and then the electrode reaction was conducted. The oxidation-reduction current generated was determined to quantify v-myc contained in the sample. As a result, v-myc could be detected in the order of pg at an improved S/N ratio when compared with conventional results.

EXAMPLE 18

Gene Detection while Inhibiting Non-Specific Adsorption of Nucleic Acid to Electrode Immobilized with Nucleic Acid Probe As a test sample, pVM 623 obtained by inserting v-myc fragment into Pst I site of pUC 119 was employed. Linear pVM 623 was obtained by digesting with Hind III and then was subjected to the thermal denaturation at 98° C. BPPG electrode immobilized with the nucleic acid probe (20 mer) having 50% homology to v-myc and BPPG electrode immobilized with the nucleic acid probe against to v-myc were placed in the test sample, which was incubated at 70° C. to effect annealing.

Then acridine orange, an intercalating agent which has specificity to the double stranded DNA and has electrode activity, was added and then the electrode reaction was conducted. The oxidation-reduction current generated was determined to quantify v-myc contained in the sample.

After this electrode reaction, -1.0 V (vs SCE) potential was applied to the electrode to remove the nucleic acid having less homology. After that, acridine orange was added similarly as above and then the electrode reaction was conducted while determining the oxidation-reduction current generated. The results indicated that the oxidation-reduction current detected from the intercalating agent when using the prove having 50% homology was about 50% of that observed when using the prove having 100% homology. Accordingly, it was clarified that variant genes can be detected by using this method.

REFERENCE EXAMPLE 5

Extraction of Nucleic Acid Using Carrier Immobilized with Double Stranded Nucleic Acid Recognizing Substance In this example, a magnetite particle having particle size of 10 μm as a carrier and aminoacridine as a double stranded nucleic acid recognizing substance were employed.

First, the magnetite particles were washed thoroughly with PBS and placed in a refluxed solution of 10% 3-aminopropyl triethoxysilane in toluene at 120° C. for 2 hours, and then washed with methanol. Subsequently, 1% glutaraldehyde solution was reacted with the particles to which then aminoacridine was immobilized.

Human leukocyte was used as a test sample. The leukocytes and the magnetic particles immobilized with aminoacridine were admixed in a plastic vessel, which was agitated vigorously by vortex mixer to effect both of cell rupture and immobilization of the nucleic acid to the carrier at once. Subsequently, a magnet was used to apply a magnetic field externally to the magnetite particles and thereby separate the particls, and the particles were washed three times with 10 mM tris buffer solution containing 200 mM NaCl (pH 7.0). After washing, the particles were placed in 70% ethanol to elute the nucleic acid.

The nucleic acid obtained was subjected to electrophoresis on 1% agarose gel, thereby obtaining the nucleic acid fragments of 20 Kb or greater, which could be cleaved with a restriction enzyme. The entire procedure could be completed within 1 hour.

As detailed above, gene detection using nucleic acid probe can be conducted conveniently within a reduced time period according to the present invention. Therefore, the present invention is extremely useful as a method for detecting a certain gene in the fields of gene diagnosis and gene engineering.

The present invention further provides a device to detect a certain gene automatically using the gene detecton sensor mentioned above.

The gene detection device according to the present invention comprises:

a gene detection sensor having a nucleic acid probe immobilized onto the surface of a carrier sensitive to physical change;

a trnasportation means to transport the gene detection sensor;

a reaction vessel to store a sample solution containing the gene sample denatured into a single stranded form, in the reaction vessel a double stranded nucleic acid being formed on the gene sensor by hybridization of the gene sample and the nucleic acid probe immobilized on the surface of the gene sensor;

a temperature control means to control the temperature of the sample solution;

a washing means to remove unreacted gene sample by washing the gene sensor after hybridization of the nucleic acid probe with the gene sample; and, a detection vessel to store a double stranded nucleic acid recognizing substance, the double stranded nucleic acid recognizing substance being reacted with the double stranded nucleic acid formed on the surface of the gene sensor in the detection vessel, whereby binding the double stranded nucleic acid recognizing substance with the double stranded nucleic acid in order to detect a physical change generated by the bound double stranded nucleic recognizing substance.

The gene sensor used in the present gene detection device may preferably be either of the electrode or optical fiber immobilized with the nucleic acid probe as mentioned above. This gene sensor may further be imparted with the function of a stirrer by forming it in the form of paddle or with the function of a temperature sensor.

The physical change such as electrochemical or optical signal detected by the gene sensor were determined directly or via appropriate controller and then further analyzed by means of computer.

In the reaction vessel, a sample solution containing the gene sample denaturated into a single strand was stored. As the sample solution, the coarse extract of the nucleic acid obtained by cell rupture may be used as it is or used after purification. A sample solution preparating device capable of preparing such coarse or purified extract of the nucleic acid may be connected to the reaction vessel and the sample solution prepared in situ from the test cells may be fed to the reaction vessel, whereby enabling full-automatic gene detection starting from the preparing the sample soulution from the test cells. The sample solution preparing device may be, for example of a disposable cartridge type, which may be exchanged to a new cartridge after completion of the determination. By using the cartridge freely replacable, the sample solution can always be prepared in a clean condition without washing.

The gene detection device according to the present invention may further be provided with a dissociation means by which double stranded nucleic acid formed on the surface of the gene sensor was dissociated into the nucleic acid probe immobilized on the gene sensor surface and the free single stranded gene sample which is removed to regenerate the gene sensor. Such dissociation means is quite desirable for the purpose of automizing the detection device since the dissociation means enables the repetitive use of the gene sensor. The dissociation means useful for the present gene detection device are the treatments with heat, bases, acids, surfactants and ultrasonic wave as mentioned above.

Furthermore, the present gene detection device may employ one or more gene sensors each immobilized with different nucleic acid probes. These gene sensors may be used at once to determine one or more items, or some of the gene sensors may be designated for a certain choice of the items to be detected.

Also, by using a plurality of gene sensors with heterogeneous nucleic acid probe immobilized thereon, a more suitable nucleic acid probe can be screened. To be more specific, a plurality of nucleic acid probe candidates are immobilized onto each of a plurality of the gene sensors, and then, the nucleic acid probe candidates immobilized on the sensor are hybridized with a nucleic acid sample. By comparing the levels of signals obtained from the sensors, the nucleic acid probe having higher affinity to the nucleic acid sample can be screened.

By taking advantage of the property that double-stranded nucleic acid is easier to dissociate as temperature increases, a more suitable probe can be obtained by conducting the hybridization at various temperatures and by screening the probe providing high signal quantum in the higher temperature. More specifically, a temperature gradient is provided by means of a temperature control device to a reaction vessel for hybridization, in which the sensors with nucleic acid probes having homologous sequences immobilized thereon are placed along the side being provided with the temperature gradient and the sensors with nucleic acid probes having heterogeneous sequences immobilized thereon are placed along the side perpendicular to that of the temperature gradient direction in the reaction vessel shown in FIG. 5. When hybridization is performed in this reaction vessel, the desirable nucleic acid probe can be readily obtained since the reactivity of the heterogeneous nucleic acid probes at the various temperatures can be simultaneously measured.

Further, by employing a base plate having a grid with at least two types of nucleic acid probes immobilized thereon, a gene can be easily detected in a short period of time. This base plate is advantageous in that the base sequence of the gene can be determined as the same time as the gene detection.

Figure 6:
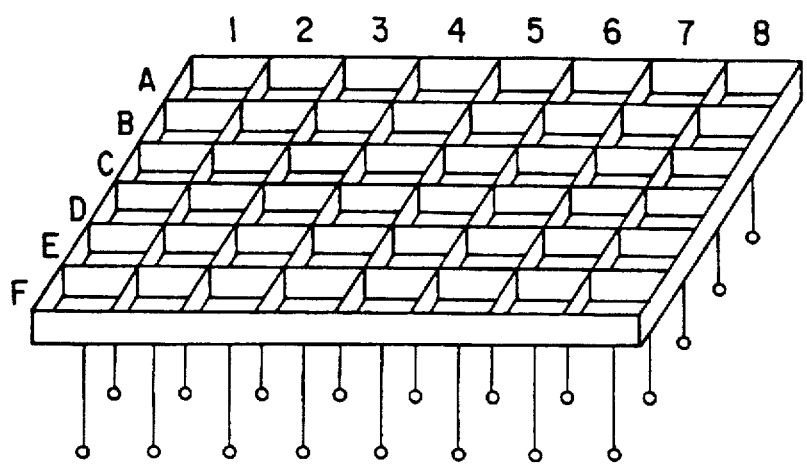
FIG. 6 shows a perspective view of a basic plate for immobilizing a nucleic acid probe used in Example 30.

The base plate used for immobilization of the nucleic acid probes is formed of a signal detectable carrier having a grid, to each box of which, nucleic acid having heterogeneous base sequence is immobilized. An example of the base plate is shown in FIG. 6. A signal detectable carrier may be a carrier which can detect the signal by itself, such as an electrode, an optical fiber, a quartz oscillator, and a semiconductor element. Besides these, a membrane such as a nitrocellulose membrane and a nylon membrane or a microtiter plate can be used. When the membrane or the microtiter is used, it is necessary to provide a signal detecting device to the rear surface of the formed base plate. Since the boxes of the grid formed by dividing the base plate at constant intervals has a discrete structure, it is free from contamination. The number of lines and rows of the grid is not particularly restricted. On the other hand, another signal detectable element can be formed when a plurality of carriers with a nucleic acid probe immobilized thereon are used in combination.

When the nucleic acid probe immobilized on the base plate is hybridized with a nucleic acid sample, each box of the grid on the base plate shows either a positive response or a negative response to the hybridization. In this way, a plurality of genes can be simultaneously examined. Moreover, if which base sequence is placed in which a box of the grid is previously known, it is possible to determine the base sequence of the nucleic acid sample by subjecting the positively-responded base sequences to a computer-analysis.

A method of detecting the gene using the gene detection device of the present invention was described below with referring the figures.

FIG. 1 shows a schematic view of an example of the automatic gene detection device according to the present invention. This device comprises three vessels, namely, reaction vessel 2, detection vessel 9 and dissociation treatment vessel 11. Reaction vessel 2 is fitted in temperature controller 3 and connected to waste tank 10, and is able to move in horizontal direction along with rail 4. Reaction vessel 2 is connected to gene sample purification device 1 at a predetermined position on rail 4. Gene sensor 5 is fixed on transportating device 12, by which horizontal transportation to the position above each tank and vertical transportation into each tank are effected. As gene sensor 5, an electrode immobilized with a nucleic acid probe is employed and the electric signals detected by this electrode is input via electric signal detection controller 6 to computer 7, by which the signals are analyzed.

The method of detecting gene using this device is as follows. First, a test cells containing the nucleic acid to be detected is placed in gene sample purification device 1, in which a test solution containing the gene samples denaturated into single strands is prepared. The sample solution thus prepared is fed to reaction vessel 2, which is then transported to the predetermined position along with rail 4. After gene sensor 5 was horizontally transported to the position above reaction vessel 2, it is transported into reaction 2. After gene sensor 5 was immersed in the sample solution in reaction vessel 2, the temperature of the sample solution was appropriately controlled by temperature controller 3 and then the nucleic acid probe immobilized to the surface of gene sensor 5 and the gene sample contained in the sample solution are hybridized. After the completion of hybridazation, gene sensor 5 is taken from the sample solution and washed with fluid fed from washing fluid vessel 8 to remove unreacted nucleic acid probe, and then the sensor is horizontally transported to the position above detection vessel 9. After removing gene sensor 5, reaction vessel 2 is transported again to the position connecting to gene sample purification device 1, and the sample solution contained is discharged to the waste tank. Gene sensor 5 transported to the position above detection vessel 9 is then transported into detection vessel 9. In detection vessel 9, a solution containing a double stranded nucleic acid recognizing substance is stored, and the double stranded nucleic acid recognizing substance recognizes and binds to the double stranded nucleic acid formed on the surface of gene sensor 5 immersed in the solution. Electrochemical signal generated by the double stranded nucleic acid recognizing substance bound to the surface is detected by gene sensor 5 and controlled by electric signal detection controller 6 and then input to computer 7 for analysis. After determination, gene sensor 5 is removed from detection vessel 9 and transported into dissociation treatment vessel 11. In dissociation treatment vessel 11, the double strands formed on the surface of gene sensor 5 is dissociated to regenerate gene sensor 5.

Reaction vessel 2 mentioned above may not necessarily be single, and combination of one or more small vessels 13 may also be employed as shown in FIG. 2. By using such one or more small vessels and one or more gene sensors 5, one or more samples can be determined at once. In such case, independent small tanks 13 may also be combined with the same number of gene sample purification devices 1 to prepare a plurality of samples at once, whereby enhancing the efficiency of the determination.

The determination can also be conducted without removing unreacted nucleic acid samples and double stranded nucleic acid recognizing substances. In such case, there is no need to provide washing fluid tank 8 and detection vessel 9, and the entire procedure through determination can be conducted in reaction vessel 2.

Furthermore, reaction vessel 2 may be a disposable reaction cell provided with a carrier immobilized with the nucleic acid probe on its bottom or side surface. The immobilized carrier useful may preferably be an electrode immobilized with a nucleic acid probe in view of the connection to the detection device body, although any other immobilized carrier listed above can be used. It is also preferable to set the immobilized carrier such a manner that it can be separated from the reaction cell for the purpose of repetitive use.

The gene detection using this reaction cell is conducted as follows. First, a sample solution containing the nucleic acid to be detected is placed in the reaction cell, which is heated to denaturate the nucleic acid to the single strand. Annealing is then conducted at a temperature selected suitably depending on the probe employed to form the double strand. The double stranded nucleic acid recognizing substance was added and the signal generated directly or indirectly is determined via the carrier provided in the reaction cell. In such case, it is not required to use the gene sensor mentioned above.

The reaction cell is separated from the detection device and discarded after every determination. Therefore, the gene detection highly reliable without cross-contamination or carry-over of the samples. In addition, the determiantion can be conducted more simply within a short period since there is no need to wash the cell.

As shown in FIG. 3, temperature controller 3 which controls the temperature of reaction vessel 2 has thermostat bath 21, controller 22 to control the temperature of thermostat bath 21, and temperature sensor 23 to determine the temperature of the sample solution. In FIG. 3, reaction vessel 2 provided in thermostat bath 21 consists of one or more small vessel 13 mentioned above. One of small vessels 13 contains a buffer solution having the composition same as that of a solution used in the sample solution, and temperature sensor 23 is inserted the buffer solution. The temperature of the buffer solution is determined as the temperature of the sample solution. Temperature sensor 23 is connected to controller 22, and it determines the temperature of the buffer solution in reaction vessel 2 and sends the data to controller 22. After receiving the temperature data from temperature sensor 23, controller 22 calculate and processes the data and then control the temperature of thermostat bath 21 to maintain the temperature of the sample solution at a certain constant level. This temperature control is preferably conducted within the range of ±0.5° C.

When the aforementioned base plate having a grid with at least two types of nucleic acid probes immobilized thereon is employed instead of a gene sensor, the device shown in FIG. 1 should be modified as follows: First, gene sensor 5 is removed from the device shown in FIG. 1. Instead of reaction vessel 2, a base plate with a nucleic acid probe immobilized thereon is provided. To the base plate, the functions equivalent to those of reaction vessel 2, detection vessel 9, and dissociation treatment vessel 11 may be provided. To be more specific, gene sample purification device 1, a solution containing a double strand nucleic acid recognizing substance, and a washing fluid supply device may be directly connected to the base plate for immobilizing a nucleic acid probe.

An example of the automatic gene detection device utilizing electrochemiluminescence is described below.

FIG. 4 shows a schematic view of an automatic gene detection device utilizing electrochemiluminescence. This device is provided with reaction cell 32 having the functions of both of reaction and detection vessels in the detection device shown in FIG. 1 and washing vessel 42. As mentioned above, it is not required to provide a reaction vessel or detection vessel separately since the determination can be conducted without removing unreacted nucleic acid probe or unreacted intercalating agent when using electrochemiluminescence. On the bottom surface of reaction cell 32, electrode 33 immobilized with a nucleic acid probe is provided. Similarly as in the reaction vessel of the detection device shown in FIG. 1, reaction cell 32 is fitted to temperature controller 34. The reaction cell is transported horizontally along with rail 35 and connected to gene sample purification device 31 at a predetermined position of rail 35. Reference electrode 36 is fixed to transporting device 12 together with the tip of optical fiber 37. By transporting device 12, reference electrode 36 and optical fiber 37 are horizontally transported and vertically transported into each vessel. Reference electrode 36 is connected to function generator/potentiostat 38 together with electrode 33 immobilized with nucleic acid probe. The potential to be applied to these electrodes is appropriately calculated by computer 39. The electrochemiluminescence generated on the surface of electrode 33 immobilized with nucleic acid probe is sent via optical fiber 37 to photomultiplier 40 for amplification and then counted by photocounter 41. The results of the determination are input to computer 39 for analysis.

The gene detection using this device is conducted as follows. First, similarly as in the case of the device shown in FIG. 1, the test cells containing the nucleic acid to be detected are placed in gene sample purification device 31 and processed into a sample solution containing the gene sample denaturated to the single strand. The solution is then transferred to reaction cell 32. Then, the temperature of the sample solution is controlled appropriately by temperature controller 34 and the nucleic acid immobilized on the surface of electrode 33 is hybridized with the gene sample in the sample solution. During this procedure, an intercalating agent capable of generating electrochemiluminescence is added to the sample solution. Alternatively, the intercalating agent may be added to the test solution prior to the hybridization. Subsequently, reaction cell 32 is transported along with rail 35 to a predetermined position and reference electrode 36 and optical fiber 37 are transported into reaction cell 32 to immerse in the sample solution. Then potential is applied between reference electrode 36 and electrode 33 immobilized with the nucleic acid provided in reaction cell 32 to generate electrochemiluminescence. The light caused by the electrochemiluminescence is brought via optical fiber 37 to photomultiplier 40 for amplification followed by counting by photocounter 41. The results of the determination are input to computer 39 for analysis. After determination, reference electrode 36 and optical fiber 37 are removed from reaction cell 32 and transferred to washing vessel 42 for washing.

EXAMPLE 19

Gene Detection Using Gene Detection Device Provided with Electrode Immobilized with Nucleic Acid Probe The automatic gene detection device shown in FIG. 1 was used to detect the gene. As a test sample, pVM 623 obtained by inserting v-myc fragment into Pst I site of pUC 119 was employed. Linear pVM 623 was obtained by digesting with Hind III and then was subjected to the thermal denaturation at 98° C. The electrode immobilized with the nucleic acid probe was placed in the test sample, which was incubated for 15 minutes at 70° C. to effect annealing. During this procedure, acridine orange, an intercalating agent which has specificity to the double stranded DNA and is electrochemically active, was added.

After the annealing, the electrode reaction was effected while determining the oxidation-reduction current produced to qunntify v-myc contained in the test sample. As a result, v-myc could be detected in pg order. The entire procedure could be conducted within 1 hour.

EXAMPLE 20

Gene Detection Using Gene Detection Device Provided with Optical Fiber Immobilized with Nucleic Acid Probe The gene was detected using the automatic gene detection device shown in FIG. 1 except for replacing gene sensor 5 and electric signal detection controller 6 with optical fiber and fluorescence detector, respectively. As a test sample pVM 623 obtained by inserting v-myc fragment into Pst I site of pUC 119 was employed. Linear pVM 623 was obtained by digesting with Hind III and then was subjected to the thermal denaturation at 98° C. The optical fiber immobilized with the nucleic acid probe was placed in the test sample, which was incubated for 15 minutes at 70° C. to effect annealing. During this procedure, acridine orange, an intercalating agent which has specificity to the double stranded DNA and is electrochemically active, was added.

After the annealing, the electrode reaction was effected while determining the oxidation-reduction current produced to quantify v-myc contained in the test sample. As a result, v-myc could be detected in pg order. The entire procedure could be conducted automatically within 1 hour.

REFERENCE EXAMPLE 6

Gene Detection Using Gene Detection Device Provided with Electrode Immobilized with Nucleic Acid Probe Utilizing Electrochemiluminescence The gene was detected by using the automatic gene detection device shown in FIG. 4. As a test sample, DNA derived from human peripheral blood admixed with pVM 623 obtained by inserting v-myc fragment into Pst I site of pUC 119 and digested with Hind III to make it linear was employed. A reaction cell provided on its bottom surface with a BPPG electrode immobilized with nucleic acid probe was prepared, and then the sample was added to this reaction cell and thermally denaturated for 5 minutes at 98° C. The sample was incubated for 15 minutes at 70° C. to effect annealing. During annealing, lucigenin which has specificity to the double stranded DNA and capable of generating electrochemiluminescence was added.

After the annealing, the electrochemical reaction was effected while counting the luminescent light by a photocounter. As a result, v-myc could be detected in pg order. The entire procedure could be conducted within 1 hour.

EXAMPLE 21

Gene Detection Using Disposable Reaction Cell Provided with Electrode Immobilized with Nucleic Acid Probe a. Preparation of reaction cell provided with electrode immobilized with nucleic acid probe (6-aminohexyl) dATP was introduced to carcinogenic gene v-myc (1.5 Kb) previously at 3' terminal using terminal deoxynuclotidyl transferase.

As an electrode to be immobilized with the nucleic acid, a Pt electrode was employed. First, the Pt electrode was heated at 180° C. for 12 hours to oxidize the surface of the electrode. The electrode was placed in a refluxed solution of 10% gamma-aminopropyl triethoxy silane in aniline at 120° C. for 30 minutes to effect silane treatment and then washed. The electrode was reacted further in 1% glutaraldehyde solution for 30 minutes and then washed. Subsequently, the electrode was reacted in a solution containing 1 µg/ml v-myc having amino group introduced at a room temperature for 30 minutes, whereby producing an electrode immobilized with the nucleic acid probe. Then a reaction cell (5×5×10 mm) provided on its bottom surface with the electrode immobilized with the nucleic acid probe was prepared.

b. Gene detection using reaction cell provided with electrode immobilized with nucleic acid probe As a test sample, the fragment obtained by digesting pVM 623 (4.6 Kb) obtained by inserting v-myc fragment into Pst I site of pUC 119 with Hind III was employed. A solution containing the segment was placed in the reaction cell produced in step a, and subjected to thermal denaturation at 95° C. for 5 minutes followed by annealing at 72° C. for 30 minutes. After reaction, tris (1,10-phenanthroline) osmium was added to the reaction cell and the electrochemiluminescence caused by applying potential to the electrode was determined. As a result, v-myc could be determined in the order of pg.

EXAMPLE 22

Gene Detection Using Disposable Reaction Cell Provided with Electrode Immobilized with Nucleic Acid Probe a. Preparation of reaction cell provided with electrode immobilized with nucleic acid probe (6-aminohexyl) dATP was introduced to carcinogenic gene v-myc (1.5 Kb) previously at 3' terminal using terminal deoxynuclotidyl transferase.

As an electrode to be immobilized with the nucleic acid, BPPG electrode was used. First, this BPPG electrode was electrolyzed in a solution containing 10% nitric acid and 2.5% potassium chromate at 2.2 V to oxidize the surface of the electrode. The electrode was placed in a refluxed solution of 10% gamma-aminopropyl triethoxy silane in aniline at 120° C. for 30 minutes to effect silane treatment and then washed with methanol. The electrode was reacted further in 1% glutaraldehyde solution for 30 and then washed. Subsequently, the electrode was reacted in a solution containing 1 µg/ml v-myc having amino group introduced at a room temperature for 30 minutes, whereby producing an electrode immobilized with the nucleic acid probe. Then a reaction cell (5×5×10 mm) provided on its bottom surface with the electrode immobilized with the nucleic acid probe was prepared.

b. Gene detection using reaction cell provided with electrode immobilized with nucleic acid probe.

As a test sample, the fragment obtained by digesting pVM 623 (4.6 Kb) obtained by inserting v-myc fragment into Pst I site of pUC 119 with Hind III was employed. A solution containing the fragment was placed in the reaction cell produced in step a, and subjected to thermal denaturation at 95° C. for 5 minutes followed by annealing at 72° C. for 30 minutes. After reaction, tris (1,10-phenanthroline) cobalt was added to the reaction cell and the oxidation-reduction potential was determined by cyclic voltammetry. As a result, v-myc could be determined in the order of pg.

As detailed described above, by using the automatic gene detection device according to the present invention, the gene can be detected automatically by the methods mentioned above. Therefore, the gene can be detected more simply within a short period.

In the detection method described above, for the purpose of providing a gene detection method capable of detecting the presence of an intended gene more safely and conveniently within a shorter period, the carriers such as an electrode or optical fiber which can detect a physical change such as electrochemical or optical signal generated from an intercalating agent is immobilized with the nucleic acid probe to use as a gene sensor. This purpose can also be achieved by using particles immobilized with the nucleic acid probe on the surface of the particles instead of the carrier immobilized with the nucleic acid probe. Thus, on the surface of the particles, the nucleic acid probe is hybridized with the gene sample to form the double strand, to which electrochemically or optically active double stranded nucleic acid recognizing substance is bound, and then the double stranded nucleic acid recognizing substance is detected electrochemically or optically by a detector.

The particles to be immobilized with the nucleic acid probe may be, but are not limited to, latex beads, polystyrene beads, glass beads, magnetic particles and the like. The diameter of the particle employed is preferably within the range from 100 A to 1 mm.

Other conditions are similar to those in cases of using the carrier such as the electrode or optical fiber immobilized with the nucleic acid probe as mentioned above.

Similarly, a filter immobilized with the nucleic acid probe on the filter surface may also be employed to detect the gene. In such case, the useful filters may be any filters as long as they do not change their nature at least at 100° C., such as, for example, those filters generally used in DNA southern blotting such as nitrocellulose filters and nylon filters. For immobilization of the nucleic acid probe onto those filters, the methods mentioned above for immobilization of the nucleic acid to a carrier can be applied as they are.

Gene detection using the filter immobilized with the nucleic acid probe can be conducted as follows.

First, a nucleic acid is extracted from a test sample such as peripheral venous blood or various organ cells according to a standard method and purified if necessary. Then a hybridization reaction solution containing the nucleic acid sample obtained is prepared and the reaction solution is applied to the multiple-layer filter device consisting of one or more filters including the filter immobilized with the nucleic acid probe, and the sample is permeated into the filter device. A double stranded nucleic acid recognizing substance, especially such a double stranded nucleic acid recognizing substance that indicates optical activity itself or via other substance, has previously been contained in the hybridization reaction solution. After the reaction solution is sufficiently permeated, the nucleic acid is thermally denaturated at 95° C. into a single strand, which is then hybridized with the nucleic acid probe immobilized on the filter surface by further heating at 37°to 72° C. After reaction, the filter immobilized with the nucleic acid probe is removed from the filter device and then washed. When the intended gene is present in the nucleic acid sample, a double strand is formed on the filter immobilized with the nucleic acid probe and this double stranded nucleic acid is bound to the double stranded nucleic acid recognizing substance. This double stranded nucleic acid recognizing substance causes the change in signal, which is determined to quantify the intended gene. Thus, when the double stranded nucleic acid recognizing substance has optical activity, then the change in optical signal such as luminescence, fluorescence, reflection, fluorescence polarization, quenching, circular dichroism and the like.

While the intended gene bound to the nucleic acid probe immobilized on the carrier is detected using the double stranded nucleic acid recognizing substance in the detection method described above, the gene can also be detected without using the double stranded nucleic acid recognizing substance by labeling the intended gene itself. For this purpose, the intended gene in the test sample is amplified as a pretreatment for the detection while labeling the primer used for amplification or starting nucleotide with a label such as electrodeactive substance or optically active substance as mentioned above. By this step, the label is introduced into the gene which has been amplified, resulting in the intended gene which has itself been labeled. The label useful for this purpose may not be particularly limited, and any substance listed above as a label capable of further binding to a biopolymer and an intercalating agent may be used.

The detection of the gene which has itself been labeled can be conducted similarly as in the detection method mentioned above except for using no double stranded nucleic acid recognizing substance.

Furthermore, the second probe in addition to the first probe which is immobilized on the carrier may be used to conduct "sandwich" hybridization, whereby detecting the intended gene without using the double stranded nucleic acid recognizing substance. Thus, the first hybridization is conducted between the first probe immobilized on the carrier and the intended gene, and then the second probe labeled is added to conduct the second hybridization with the intended gene bound to the first probe followed by the detection of the signal from the label of the second probe.

The second probe useful may any nucleic acid having the base sequence complementary to the intended gene to be detected. When the intended gene has one or more base sequences complementary to the first probe then the first probe can be used as the second probe.

The label to be used to label the second probe may not particularly be limited, and the substances listed above as the labels capable of binding further to a biopolymer and an intercalating agent may be used.

In this gene detection method, the process to the step of hybridization of the first probe immobilized on the carrier with the intended gene may be similar to that in the detection method using the double stranded nucleic acid recognizing substance as mentioned above. After the first probe is bound to the intended gene, the second probe is added instead of the double stranded nucleic acid recognizing substance, and then the second hybridization is conducted under the condition similar to that of the first hybridization. The second probe may also be added before the first hybridization. After the completion of the second hybridization, the gene is detected by a suitable method depending on the label introduced to the second probe. Specifically, the method of detecting the double stranded nucleic acid recognizing substance bound to the double strand can be used as it is.

Most of the genetic diseases are developed when a particular base sequence is defected or combination of a plurality of particular base sequences are presented in a gene. Thus, most of the genetic diseases can not be identified directly by using the nucleic acid probe. Accordingly, most of the diseases are now identified by using restriction fragments length polymorphism (RFLP) analysis. This RFLP method involves an analysis of the pattern of DNA fragments and thus requires the procedure of separating the DNA fragments. Presently, the separation of DNA fragments employs only electrophoresis which involves the problem of complicated procedures and a long time period for the determination.

Such analysis of the pattern of DNA fragments can be conducted conveniently within a short period by using the gene detection method of the present invention in the procedure described below.

First, DNA is extracted from a biological material and then digested with an appropriate restriction enzyme. The restriction enzyme useful is not particularly limited and any enzyme generally used in RFLP may be employed. Examples of the useful restriction enzyme are AccI, AvaI, BamHI, HincII, HindIII, PstI, BalI, NsiI, HaeII, EcoRI, and MspI.

The DNA fragments obtained are then separated based on molecular weights electrophoresis, gel electrophoresis and the like agarose gel electrophoresis, polyacrylamide electrophoresis, pulsefield electrophoresis, capillary electrophoresis, high performance liquid chromatography (HPLC) such as FPLC (manufactured by PHARMACIA Co., Ltd.). DNA fragment may also be separated after denaturated by, for example, heating at 90°to 98° C.

Then DNA fragments separated based on molecular weights are hybridized with the nucleic acid probe immobilized onto the carrier. This hybridization may be conducted in a flow system of a constant flow rate or in a series of fractions having the same volume.

When the hybridization is conducted in the flow system, the conditions such as temperature and pH of moving phase are suitably selected depending on the hybridization reaction. The composition of the moving phase is not particularly limited although a salt concentration of about 0 to 1M, pH of the neutral region, and a temperature within the range from 37°to 72° C. are preferred. While it is desirable to add the double stranded nucleic acid recognizing substance previously to the sample solution, it is also acceptable that a carrier having the double strands formed on the surface is placed in a solution containing the double stranded nucleic acid recognizing substance. As a double stranded nucleic acid recognizing substance, any of those listed above may be employed. In the flow system, the time period (retention time) between the introduction of the sample solution and the generation of the direct or indirect signal from the double stranded nucleic acid recognizing substance is determined. The pattern of DNA fragments based on, for example, RFLP can be obtained.

When the hybridization is conducted after obtaining the fractions, each fraction is subjected to the hybridization with the nucleic acid probe immobilized to the carrier and then the double stranded nucleic acid recognizing substance is added to the fraction to determine the direct or indirect signal from the double stranded nucleic acid recognizing substance. From the fraction number of the fraction in which the signal is obtained, the pattern of DNA fragments based on, for example, RFLP can be obtained.

Although the present invention is a method to detect the presence of a gene having a particular base sequence as mentioned above, the present method can further enable the separation of the gene having the particular base sequence. Specifically, since in the detection method mentioned above the intended gene is immobilized to a carrier by means of hybridization with the nucleic acid probe, the intended gene can be separated from the test sample only by removing the carrier from the test sample. Accordingly, the intended gene can exclusively separated by dissociating the intended gene from the carrier by an appropriate means after removing the substrate.

More specifically, this gene separation can be performed by first hybridizing the nucleic acid probe immobilized on the carrier gene surface with the intended gene to form a double stranded nucleic acid, to which then the double stranded nucleic acid recognizing substance added before or after hybridization is bound, and then by detecting the signal from the double stranded nucleic acid recognizing substance bound to the double stranded nucleic acid to confirm the presence of the intended gene. Then the carrier on which the presence of the intended gene has been confirmed is removed from the test sample to separate the intended gene from the test sample, and then by means of thermal or alkaline denaturation the intended gene is dissociated from the carrier. In this gene separation method, the procedure to the step of detecting the intended gene contained in the test sample is similar to that in the gene detection method mentioned above.

To dissociate the intended gene from the carrier, the carrier may be heated at a temperature of 95° C. or higher in a buffer solution or may be exposed to an alkaline condition using for example sodium hydroxide. By this procedure, the intended gene is separated in a form of a single strand.

The gene thus obtained is converted to a double strand by synthesizing a complementary chain using an enzyme. The yield may be increased by amplification using an enzyme. Especially by PCR method, the yield can be increased while forming a double strand at a same time. By forming a double strand which is then incorporated via a linker into a vector, the intended gene can be cloned efficiently and easily.

REFERENCE EXAMPLE 7

Gene Detection Using Latex Beads Immobilized with Nucleic Acid Probe a. Introduction of amino group into nucleic acid probe (6-aminohexyl) dATP was introduced to a carcinogenic gene v-myc at its 3' terminal by using terminal deoxynucleotidyl transferase.

b. Immobilization of nucleic acid probe to latex beads

A single stranded nucleic acid probe was immobilized to the latex beads of the particle size of 1 μm using dicyclohexylcarbodiimide as a crosslinking agent. The latex beads immobilized with the nucleic acid probe was heated at 98° C. in a solution of the sample (containing v-myc) to effect thermal denaturation followed by hybridization at 72° C. for 15 minutes. Acridine orange solution was added to this solution, which was then allowed to stand for 1 minute. After washing at 72° C. with washing fluid (2×SSC, 0.1% SDS), intensity of fluorescent light was determined in a phosphate buffer solution. As a result, the gene could be detected in the order of pg.

REFERENCE EXAMPLE 8

Gene Detection Using Latex Beads Immobilized with Nucleic Acid Probe a. Introduction of amino group into nucleic acid probe (6-aminohexyl) dATP was introduced to a carcinogenic gene v-myc at its 3' terminal by using terminal deoxynucleotidyl transferase.

b. Immobilization of nucleic acid probe to latex beads

A single stranded nucleic acid probe was immobilized to the latex beads having the particle size of 1 μm using dicyclohexylcarbodiimide as a crosslinking agent. The latex beads immobilized with the nucleic acid probe was heated at 98° C. in a solution of the sample (containing v-myc) to effect thermal denaturation followed by hybridization at 72° C. for 15 minutes. Acridine orange solution was added to this solution (final concentration of 1 μM) which was then allowed to stand for 1 minute. Then the oxidation-reduction current of the intercalating agent in the solution was determined. As a result, the gene could be detected in the order of pg.

REFERENCE EXAMPLE 9

Gene Detection Using Filter Immoblized with Nucleic Acid Probe

As a nucleic acid probe, a carcinogenic gene v-myc was selected. This v-myc was bound to aminoacridine via glutaraldehyde and the further immobilized to PVDF nylon filter by UV irradiation. After immobilization of the nucleic acid probe, non-specific adsorption to the filter surface was suppressed by treatment with 1 mg/ml ATP solution.

The sample solution containing v-myc was heated at 98° C. to effect the thermal denaturation, followed by hybridization with the nucleic acid probe immobilized to the filter surface at 72° C. for 15 minute. After reaction, the filter was washed at 72° C. (2×SSC, 0.1% SDS) and the change in adsorbance on the surface of the filter was determined.

In the case that the intended gene was present in the sample, reduction in absorbance was observed. As a result of the determination, the gene could be detected in the order over 10 pg.

After the similar treatment, the change in intensity of fluorescent light on the filter surface was also determined. As a result, in the cases that the intended gene was present in the sample, increase in intensity of fluorescent light was observed. As a result of the determination, the gene could be detected in the order over 10 pg.

REFERENCE EXAMPLE 10

Gene Detection Utilizing Sandwich Hybridization a. Preparation of electrode immobilized with first nucleic acid probe A synthetic oligonucleotide probe (20 mer) against to the carcinogenic gene v-myc was used as the first probe, to which (6-aminohexyl) dATP was introduced at 3' terminal using terminal deoxynucleotidyl transferase.

On the other hand, BPPG electrode was electrolyzed in a solution containing 10% nitric acid and 2.5% potassium chromate at 2.2 V to oxidize the surface. The electrode whose surface had been oxidized was then placed in a refluxed solution of 10% gamma-aminopropyltriethoxysilane in aniline at 120° C. for 30 minutes to effect silane treatment. The electrode treated with silane was washed with methanol and reacted in 1% glutaraldehyde solution for 30 minutes, and then washed again.

The electrode was reacted in a solution of 1 μg/ml of the first probe to which amino group had been introduced at a room temperature for 30 minutes, whereby producing an electrode immobilized with the first nucleic acid probe.

The electrode immobilized with the first nucleic acid probe thus obtained was immersed in a solution of nucleotides (dATP, dCTP, dGTP and dTTP) so that the nucleotides were adsorbed to the surface of the electrode to suppress non-specific adsorption of the sample DNA.

b. Gene detection using second nucleic acid probe

A fragment of pVM 623 obtained by inserting v-myc fragment to Pst I site of pUC 119 was digested with Hind III. The fragment thus obtained was used as a test sample and Pst I fragment of pUC 119 was used as the second probe. The second probe was labeled with viologen.

The test sample and the second probe were thermally denaturated at 98° C. The BPPG electrode immobilized with the first probe prepared in step a was placed in a solution containing the test sample and the second probe, which was then incubated at 70° C. to effect annealing. During the annealing, 0.1 V of potential (vs. SCE) was applied to the electrode. After annealing, negative potential was applied to the electrode to remove the substance binding non-specifically to the electrode. The oxidation-reduction potential of viologen labeled to the second probe was then determined to quantify v-myc contained in the test sample. As a result, v-myc could be detected in the order of pg.

EXAMPLE 23

Indirect Gene Detection by RFLP Analysis Using Electrode Immobilized with Nucleic Acid Probe Using an electrode immobilized with the nucleic acid probe, the individual identification by DNA fingerprint method was conducted as follows.

First, leukocytes were separated from human peripheral venous blood by density gradient centrifugation and DNA was extracted according to a standard method. Then DNA obtained was digested with a restriction enzyme Hae III.

On the other hand, Myo probe was immobilized to BPPG electrode to prepare an electrode immobilized with the nucleic acid probe, which was then fitted to the outlet of the column of high pressure liquid chromatograph (HPLC). By loading the sample to HPLC, DNA including the sequence having homology to the probe immobilized to the electrode surface was supported temporarily on the electrode surface to form a double strand, to which then the double stranded nucleic acid recognizing substance such as an intercalating agent was bound, whereby enabling the determination of electrochemical signal from the double stranded nucleic acid recognizing substance. The signals obtained exhibit a specific pattern. By analyzing this pattern, the patterning of the sample can be conducted.

By thermally denaturating the fragment of DNA obtained as above at 95° C. to obtain a single strand, which was then subjected to HPLC together with a intercalating agent, acridine orange, to conduct the patterning of DNA. During chromatography, the column was maintained at 75° C.

The results obtained indicated the discrete patterns by individuals subjected to the study. Accordingly, it was clearly indicated that individual identification is possible by the present gene detection method.

REFERENCE EXAMPLE 11

Gene Separation Using Electrode Immobilized with Nucleic Acid Probe

A solution of chromosomal DNA (10 μg/ml) extracted from E. coil strain JM 109 admixed with of 1 μg/ml digested pVM 623 (obtained by inserting v-myc to pUC 119) with Hind III was used as an experimental model system. The sequence 5'-TGCAGTTCCGGTGGCTGATC-3' (SEQ ID NO: 19) in v-myc was used as a probe for detection and separation.

a. Preparation of BPPG electrode immobilized with nucleic acid probe

BPPG electrode was electrolyzed in a solution of 2.5% potassium chromate and 10% nitric acid at 2.2 V for 10 seconds to oxidize the surface. The electrode was placed in a refluxed solution of 10% gamma-aminoprpyltriethoxy silane in toluene at 120° C. for 30 minutes to effect silane treatment. By this treatment, amino group was introduced to the electrode surface. Then the electrode was allowed to stand in 1/15M phosphate buffer (pH 7.0) containing 1% glutaradldehyde for 1 hour at a room temperature to introduce aldehyde group. The synthetic primer mentioned above was prepared into a solution of 10 μg/ml in 10mM phosphate buffer, in which the electrode treated with aldehyde was then placed and allowed to stand for 1 hour at a room temperature. In this step, the primer was immobilized on the electrode surface.

b. Detection of intended gene

The BPPG electrode immobilized with the nucleic acid probe prepared in step a was placed in a solution of chromosomal DNA (10 μg/ml) extracted from E. coil strain Jm 109 admixed with of 1 μg/ml of pVM 623 which had been converted to a linear form by using Hind III and was hybridized at 55° C. An intercalating agent, acridine orange, was added to obtain the concentration of 1 μM and then the electrode response was determined.

As a result, the peaks specific to acridine orange were obtained, indicating the formation of the double strands on the electrode surface.

c. Separation of intended gene

The electrode was removed from the sample solution and heated at 95° C. in the buffer to dissociate the intended gene in a double strand form. Then 5'-TGCAGTTCCGGTGGCTGATC-3'(SEQ ID NO: 20) and 5'-CGACTCGGAAGAAGAACAAG-3' (SEQ ID NO: 21) which were the fragments in v-myc were used as the primers to conduct PCR. The length between the base sequences complementary to the two primers is about 900 bp. The gene amplified by PCR was subjected to electrophoresis, in which the band corresponding to 900 bp was observed, whereby confirming the separation of pVM 623 which was intended to be separated.

As a control, the same procedure was taken using pUC 118 as an intended gene and the base sequence in pUC 118 as a PCR primer, and no band was observed at the corresponding position.

EXAMPLE 24

Gene Detection Using Electrode Immobilized With Nucleic Acid Probe and Blocked by Stearylamine a. Preparation of electrode immobilized with nucleic acid probe (6-aminohexyl) dATP was introduced at 3' terminal into synthetic oligonucleotide probe (20 mer) against to a carcinogenic gene v-myc using terminal deoxynuclotidyl transferase.

On the other hand, BPPG electrode was subjected to electrolysis at 2.2 V in a solution containing 10% nitric acid and 2.5% potassium chromate to oxidize the surface of the electrode. The electrode whose surface had been oxidized was then placed in a refluxed solution of 10% gamma-APTES in aniline at 120° C. for 30 minutes to effect silane treatment. After the silane-treated electrode was washed with methanol, it was reacted in 1% glutaraldehyde solution for 30 minutes, and then washed again.

This electrode was reacted in a solution containing 1 μg/ml of the probe to which amino group had been introduced at a room temperature for 30 minutes, whereby producing an electrode immobilized with the nucleic acid probe.

This electrode was immersed in a stearylamine solution to adsorb stearyamine on the surface of electrode, thereby a non-specific adsorption of a sample was suppressed.

b. Gene detection using electrode immobilized with nucleic acid probe

As a test sample, pVM 623 obtained by inserting v-myc fragment into Pst I site of pUC 119 was employed. Linear pVM 623 was obtained by digesting with Hind III and then was subjected to the thermal denaturation at 98° C. The BPPG electrode immobilized with the nucleic acid probe produced in step a above was placed in the test sample, which was then incubated at 70° C. to anneal. Subsequently, an intercalating agent acridine orange which binds specifically to the double stranded nucleic acid and has electrode activity was added and then the electrode reaction was conducted, during which the oxidation-reduction current generated was determined to quantify v-myc contained in the test sample.

As a result, v-myc could be detected in the order of pg. S/N ratio observed was higher than that of the electrode whose surface was not blocked.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

Hereinbefore, described is the gene detection method using the carrier with a nucleic acid probe immobilized thereon. In a modified method of the present invention, a gene can be detected by the use of a carrier with a nucleic acid sample instead of a nucleic acid probe immobilized thereon.

To be more specific, a gene can be detected by the gene detection method which comprises the steps of identifying the presence of a gene of interest by reacting a single-stranded nucleic acid probe having a base sequence complementary to the gene of interest with a nucleic acid sample denatured to a single-strand form;

performing hybridization of the nucleic acid probe and the nucleic acid sample; and detecting the presence of the double-stranded nucleic acid formed as a result of the hybridization, and, which further comprises the steps of, using the nucleic acid sample by immobilizing on the electrode surface or on an end of optical fiber;

adding an electrochemically or photochemically active double strand recognizing substance which binds specifically to a double-stranded nucleic acid, to the reaction system of a nucleic acid sample and the nucleic acid probe; and detecting the double strand recognizing substance immobilized on the electrode or to the optical fiber by means of an electrochemical or a photochemical determination method via the electrode or the optical fiber.

In the gene detection method, the fact that the presence of the double strand recognizing substance immobilized on an electrode or an optical fiber is detected, indicates that a double-stranded nucleic acid has been formed on the surface of the electrode or the optical fiber as the same as the detection method using the carrier with the nucleic acid probe immobilized thereon. This fact further means that the nucleic acid sample immobilized on the electrode or the optical fiber is the gene of interest.

This method can be performed in substantially the same manner as in the aforementioned method of the present invention since the nucleic acid sample instead of the nucleic acid probe, is immobilized on the carrier.

As the double strand recognizing substance and the nucleic acid probe to be used in the present invention, a double strand recognizing substance such as the aforementioned intercalating agents and bipolymer, and a nucleic acid probe can be used. Further, the condition including the amount of the double strand recognizing substance, the length of the nucleic acid probe, and labelling of the double strand recognizing substance is the same in the present invention.

The nucleic acid sample to be immobilized on the carrier can be prepared from the aforementioned test sample, which can be also extracted in the same manner as the above. The extracted test sample can be amplified in the same manner as described above prior to preparing the nucleic acid sample. Thus obtained nucleic acid is denatured to a single strand form according to the aforementioned method.

In this method, the nucleic acid sample is extracted from the test sample, denatured to a single strand form, and immobilized on a carrier. The method for immobilizing the nucleic acid sample on the carrier is the same as in that for immobilizing the nucleic acid probe on the carrier. The nonspecific adsorption of a nucleic acid, a double strand recognizing substance, and the like to the carrier with the nucleic acid sample immobilized thereon can be suppressed in the same manner as in the method for immobilizing the nucleic acid probe on the carrier. The amount of the nucleic acid sample immobilized on the carrier is not particularly restricted. However, when the nucleic acid sample is immobilized in a high density, the detection can be made with a higher sensitivity, as a result, a S/N ration increases. The density of the nucleic acid sample to be immobilized is generally of the order of amol/cm$^2$ or higher, preferably the order of nmol/cm$^2$ or higher.

The RFLP analysis can be performed by the method using the carrier with the nucleic acid sample immobilized thereon. To be more specific, the RFLP analysis is performed in the following steps of eluting each gene fragment obtained from the aforementioned molecular weight gene fractionation from the carrier used for the fractionation according to the aforementioned method;

denaturing the fragment with alkali or on heating to a single-stranded fragment;

immobilizing the fractionated gene fragment depending on the molecular weight on the carrier capable of detecting an electrochemical or a photochemical signal. The determination of a signal requires a long time in a conventional method due to an intricate operation procedure containing the following steps of performing the molecular weight fractionation of the gene fragment by means of electrophoresis;

transferring the fractionated fragment to a filter by blotting;

hybridizing with radioisotope-labeled probe;

identifying the presence of hybridized bands in the radioautograph; and analyzing the electrophoresis pattern characteristic of the specific disorder.

In contrast, according to the method of the present invention detecting a signal electrochemically or photochemically, the RFLP analysis of the specific gene can be readily performed.

As the carrier for immobilizing the gene fragment, any carrier which is employed in immobilizing the single-stranded nucleic acid sample can be used. However, for the RFLP analysis, a tape-formed carrier is preferably used. When the tape-formed carrier is used, as soon as the fractionated gene fragment is eluted from the carrier used for fractionation, the double-stranded fragment is allowed to dissociate to a single strand form at the end of the carrier. At the same time, the dissociated single-stranded fragment is immobilized on the tapeform carrier by being sliding horizontally at the same speed as the elution rate. Therefore, the elution and the immobilization of the gene can be carried out simultaneously. In addition, the fractionated gene depending on the molecular weight can be immobilized in molecular weight order along the tape-sliding direction. Therefore, the tapeform carrier is advantageous that the RFLP of a specific gene can be more easily obtained and the detection of the gene after the molecular weight fractionation can be more easily carried out.

The nucleic acid sample immobilized on an electrode or on the surface of an optical fiber can be quantified by measuring the oxidation-reduction current or the optical signal of a nucleic acid or of an electrochemically or an optically active substance which binds specifically to a single-stranded nucleic acid. To be more specific, in the case that the carrier is an electrode, the immobilized nucleic acid can be quantified by measuring the oxidation-reduction current from the nucleic acid or the intercalating agent by means of determination system consisting of a potentiostat, a function generator, a recorder, and a computer. In the case that the carrier is an optical fiber, the quantification of the nucleic acid is conducted by measuring an optical signal such as, adsorbance, fluorescence intensity, luminescence, quenching, circular dichroism, fluorescence polarization, or other optical parameters by means of a determination device corresponding to each optical parameter. As the oxidation-reductive current from a nucleic acid, the oxidative-reduction current from adenine, thymine, guanine, or cytosine can be utilized in the same manner as in the aforementioned present invention.

In this gene detection method, the electrode or the optical fiber with the nucleic acid sample immobilized thereon is placed in a solution dissolving the nucleic acid probe and hybridization is performed in a temperature range of 37° to 72° C. The optimal temperature of the hybridization reaction varies depending on the base sequence and the length of the probe to be employed.

In this gene detection method, in the case that the electrode with the nucleic acid sample immobilized thereon is employed, the hybridization reaction can be facilitated by applying an electric potential on the surface of the electrode before and/or during the reaction. The electric potential to be applied is the same as in the aforementioned method using the nucleic acid probe. Also, by applying a negative potential to the electrode after the hybridization reaction, the non-specifically adsorbing nucleic acid can be removed.

The double strand recognizing substance can be added to the test sample either before or after the hybridization reaction. Alternatively, a solution containing the double strand recognizing substance is prepared, to which the electrode or the optical fiber with the nucleic acid sample immobilized thereon may be inserted after hybridization reaction. When the carrier is the electrode, non-specific adsorption of the double strand recognizing substance to the carrier can be suppressed by applying a positive electric potential since the double strand recognizing substance is generally charged positively.

The presence of the double-stranded nucleic acid formed on the electrode or to the optical fiber can be detected by determining the presence of the double strand recognizing substance immobilized on the electrode or the optical fiber. As a determination method, the same method as in the case of using the immobilized nucleic acid probe is employed. To be more specific, when the electrode with nucleic acid sample immobilized thereon is employed, the determination is carried out by means of the determination system consisting of a potentiostat, a function generator, and a recorder by applying the electric potential at the level within the vicinity of the oxidation-reduction potential of an intercalating agent. The gene can be quantified by determining the level of the oxidation-reduction current. Since the electrode reaction occurs only on the surface of the electrode, the electrode response of the intercalating agent bound to the double-stranded nucleic acid can be obtained exclusively upon occurrence of the hybridization. The electrochemical determination may be performed in a test sample solution or in other electrolysis solutions. It may also be carried out in a hydrophilic, or hydrophobic solvent.

When the optical fiber with nucleic acid sample immobilized thereon is employed, the gene of interest is quantified by determining the optical parameter such as adsorbance, luminescence, fluorescence, reflection, quenching, circular dichroism, and fluorescence polarization.

In this detection method, nucleic acid sample may be immobilized on a particle instead of on the electrode or to the optical fiber in the same manner as in the case of using the immobilized nucleic acid probe. To be more specific, first the nucleic acid sample is hybridized with nucleic acid probe on the surface to the particle to form a double strand nucleic acid, and then, to which electrochemically or photochemically active double strand recognizing substance is allowed to bind. The double strand recognizing substance may be detected electrochemically or photochemically.

As a particle with the nucleic acid sample immobilized thereon, the same particle as used in the aforementioned case using the immobilized nucleic acid probe can be used. The condition e.g., the diameter of the particle etc., is also similar to the above.

Further, a filter with the nucleic acid sample immobilized on the surface my be made of the same material and in the same condition as in the aforementioned case using filter with the nucleic acid probe immobilized thereon. The procedure will be more specifically explained hereinbelow.

First, a nucleic acid is extracted form the test sample such as peripheral venous blood, cells of various organs according to the conventional method. The extracted nucleic acid can be purified, if necessary. Thus obtained nucleic acid sample is immobilized onto a filter. Then, manufactured is a multi-layered filter device consisting of a plurality of filters including the filter with the nucleic acid sample immobilized thereon. On the other hand, a reaction solution for use in hybridization containing a nucleic acid probe is prepared. The reaction solution is added to the filter device to allow the nucleic acid probe to penetrate into the filter device. To the reaction solution for use in hybridization, the double strand recognizing substance, preferably the double strand recognizing substance having direct or indirect optical activity has been added. After allowing the reaction solution sufficiently to penetrate into the filter device, the hybridization of the nucleic acid probe and the nucleic acid sample immobilized on the surface to the filter is carried out on heating in a temperature range of 37°to 72° C. After the completion of the hybridization, the filter with the nucleic acid probe immobilized thereon is removed form the filter device and washed. When a gene of interest is present in the nucleic acid sample, a double strand is formed on the filter with the nucleic acid sample immobilized thereon. The double strand recognizing substance is bound to the double strand form. The gene of interest is quantified by determining a change in a signal level generated from the double strand recognizing substance. When the double strand recognizing substance has an optical activity, a change in an optical parameter such as luminescence, fluorescence, reflection, fluorescence polarization, quenching, and circular dichroism may be determined.

The gene detection method using the electrode or the optical fiber with the nucleic acid sample immobilized thereon can be carried out in a batch system or an automatic system by use of a gene detection device which comprises:

a carrier selected from the group consisting an electrode and an optical fiber for immobilizing a nucleic acid sample on the surface thereof;

a transportation means to transport the carrier;

an immobilization vessel in which a sample solution containing a nucleic acid sample denatured to a single strand form is stored, and in which the nucleic acid sample is immobilized on the surface of the carrier;

a reaction vessel in which a probe solution containing the nucleic acid probe is stored, and in which the nucleic acid sample immobilized on the surface of the carrier is hybridized with the nucleic acid probe to form the double-stranded nucleic acid on the carrier;

a temperature control means to control the temperature of the probe solution;

a washing means to remove an unreacted nucleic acid probe by washing the carrier after the hybridization with the nucleic acid probe; and a detection vessel in which the double strand recognizing substance is stored, and in which the double-stranded nucleic acid formed on the surface of the carrier is allowed to react with the double strand recognizing substance in the solution to form the double strand recognizing substance bound to the double-stranded nucleic acid, whose electrochemical or photochemical signal is detected.

In the aforementioned gene detection device, a test solution containing the nucleic acid sample denatured to a single-strand form is stored in the immobilization vessel. As the sample solution, a crude nucleic acid solution extracted from the test cell homogenate may be used as it is or in purified form. If a sample solution preparation device for preparing the crude solution or the purified solution of the nucleic acid extract is connected to the immobilization vessel, the sample solution obtained from the test cell homogenate can be directly transported to the immobilization vessel, with the result that gene detection can be automatically performed starting from the test cell homogenization. In this case, a cartridge-type disposable device is preferable as the sample solution preparation device. The cartridge-type device may be replaced with a new cartridge after completion of the determination. By employing the free-placeable-and-removable cartridge-type device, the sample solution can be prepared always in a clean condition without washing.

To the aforementioned gene detection device, a removal means to remove the double-stranded nucleic acid formed on the surface of the carrier can be provided to regenerate the carrier. Such a removal means can make it possible to use the carrier repeatedly and is very desirable to realize an automatic gene detection device. As the removal means to be used in the aforementioned gene detection device, treatment with a substance having a low relative permitivity such as chloroform, a caotropic agent such as potassium iodide, and surfactant may be mentioned. In addition, heating can be helpful to reduce the period of time of removing the nucleic acid sample. As an alternative method, nuclease such as DNase and RNase can be used to remove the nucleic acid sample from the carrier.

In the aforementioned gene detection device, a plurality of carriers can be used.

Hereinbelow, the automatic gene detection device by use of the gene detection method using a carrier with a nucleic acid sample immobilized thereon will be explained with reference to drawings.

FIG. 7 is a view schematically illustrating an automatic gene detection device by use of the gene detection method of the present invention. This device comprises 4 types of vessels, namely, immobilized vessel 52, reaction vessel 54, detection vessel 60, and removal treatment vessel 62. Immobilized vessel is connected to waste tank 61, and is able to be horizontally transported along rail 53. When immobilized vessel 52 is transported at a predetermined position, it is connected to nucleic acid sample purification device 51. In immobilized vessel 52, a nucleic acid sample is immobilized on carrier 56. Reaction vessel 54 is placed in temperature controller 55. Carrier 56 is immobilized on transporting device 63, by which carrier 56 can be horizontally transported to a predetermined position above each vessel and can be vertically transported into each vessel. As carrier 56, an electrode or an optical fiber is used. The electric signal detected by carrier 56 is input via electric signal detection control device 57 into computer 58 for analysis.

Hereinbelow, the gene detection method using this device will be explained. First, test cells containing the nucleic acid of interest are placed in nucleic acid sample purification device 51, in which a sample solution containing nucleic acid sample denatured to a single-strand form is prepared. The prepared sample solution is transported to immobilized vessel 52, which is then transported to a predetermined position along on rail 53. After horizontally transported to the position above immobilized vessel 52, carrier 56 is transported into immobilized vessel 52. Carrier 56 is allowed to immerse in the sample solution stored in immobilized vessel 52 and the nucleic acid sample is allowed to adsorb on the surface of carrier 56. Thereafter, carrier 56 is removed from immobilized vessel 52 and horizontally transported to the position above reaction vessel 54. After carrier 56 is removed, immobilized vessel 52 is again transported to the position which can be connected to nucleic acid sample purification device 51, and the sample solution remaining in the device 51 is allowed to discharge to waste tank 61. On the other hand, carrier 56 which is transported to the position above reaction vessel 54 is then transported into reaction vessel 54. In reaction vessel 54, in which a nucleic acid probe has been previously placed, hybridization of the nucleic acid sample immobilized on carrier 56 and the nucleic acid probe is performed. The hybridization reaction proceeds by controlling the temperature of the probe solution to an optimal value by means of temperature controller 55. After completion of the reaction, carrier 56 is removed from the probe solution and washed with a washing fluid supplied from washing fluid tank 59 to remove unreacted nucleic acid probe, and then horizontally transported to the position above detection vessel 60. Carrier 56 transported to the position above detection vessel 60 is then transported into detection vessel 59. In detection vessel 60, stored is a solution containing double strand recognizing substance, which can recognize and bind to the double stranded nucleic acid formed on the surface of carrier 56 which is immersed in the solution. The electrochemical signal generated from the double strand recognizing substance bound to the double-stranded nucleic acid can be detected by carrier 56. the signal detected by carrier 56 is input to computer 58 for analysis after being controlled by electric signal detection control device 57. After completion of the determination, carrier 56 is removed from detection vessel 60 and transported to removal treatment vessel 62, in which the double strand formed on the surface of carrier 56 is removed to regenerate carrier 56.

The aforementioned reaction vessel 54 may not necessarily be a single vessel, and a plurality of small vessels 13 may also be used in combination as shown in FIG. 2 as described in explanation of the detection method using the carrier with a nucleic acid probe immobilized thereon. By using the reaction vessel and a plurality of carriers 56, a plurality of samples can be simultaneously determined. In this case, by preparing a plurality of samples using small vessels 13 together with the equal number of nucleic acid sample purification devices 51, the determination of the samples can be efficiently performed.

On the other hand, the determination can be carried out without removing unreacted nucleic acid probes and double strand recognizing substances. In this case, washing fluid tank 59 and detection vessel 60 are not required and the determination can be performed in reaction vessel 54.

Furthermore, as reaction vessel 54, a disposable reaction cell provided with a carrier having the nucleic acid sample immobilized on the inner bottom or the inner side surface may be used. As the carrier used for immobilizing the nucleic acid sample, although any carrier mentioned above can be used, an electrode with the nucleic acid sample immobilized thereon is preferable in view of the availability of connection with the detection device body. The carrier for use in immobilization can be placed at the reaction cell as a removable discrete unit so as to use repeatedly.

The gene detection using this reaction cell is performed as follows. First, the nucleic acid sample is immobilized onto the carrier placed in the reaction cell according to the aforementioned method. Second, a solution containing a nucleic acid probe is added to the reaction cell. After annealing is conducted to form a double strand at a temperature suitable for a probe to be used, the double strand recognizing substance is added thereto. The signal generated directly or indirectly from the double strand recognizing substance is determined through the carrier placed in the reaction cell. In this case, it is not necessary to use another carrier since the reaction cell has the carrier with the nucleic acid sample immobilized thereon.

The reaction cell is removed from the detection device and discarded after every determination. Therefore, the gene detection can be carried out with high reliability since there is no risk of cross contamination or carry-over of the samples. Besides this, since the disposable reaction cell eliminates a washing process, the determination can be carried out more simply in a short period of time.

As temperature controller 55 to control the temperature of reaction vessel 54, the same temperature controller as in the method using the carrier with the nucleic acid probe immobilized thereon. To be more specific, the device as shown in FIG. 3, having thermostat bath 21, temperature controller 22 to control the temperature of the thermostat bath 21, and temperature sensor 23 to determine the temperature of a test solution may be used. Reaction vessel 2 shown in FIG. 3, disposed in thermostat 21 is formed by use of a plurality of small vessels 13 in combination. A buffer solution having the same composition as that of the probe solution is stored in one of small vessels 13. Temperature sensor 23 is inserted in the buffer solution to determine the temperature, which is regarded as the temperature of the probe solution. Temperature sensor 23 is connected to controller 22. The temperature of the buffer solution in reaction vessel 2 determined by temperature sensor 23 is transmitted to controller 22, in which the temperature information is computer-analyzed and control the temperature of thermostat vessel 21 so as to maintain the probe solution at a predetermined temperature. The temperature is controlled preferably in a range of ±0.5° C.

As mentioned above, when the carrier with the nucleic acid sample immobilized thereon is used, a gene of interest can be detected by use of electrochemical luminescence in the same manner as in the case of using the carrier with the nucleic acid probe immobilized thereon. Hereinbelow, an example of the gene detection device using electrochemiluminescence will be described.

FIG. 8 is a view of schematically illustrating the gene detection device using electrochemiluminescence. This device has reaction cell 73 having the functions equivalent to those of immobilizing vessel, reaction vessel, and detection vessel as shown in FIG. 7, and washing vessel 83. As mentioned above, since the determination of the sample can be carried out without removing unreacted nucleic acid probes and an unreacted intercalating agent when electrochemiluminescence is used, an independent reaction vessel and detection vessel are not required. On the surface of the bottom of reaction cell 73, electrode 74 for immobilizing the nucleic acid sample is provided. Reaction cell 73 is disposed in temperature controller 75 as in the same fashion as in the reaction vessel of the detection device shown in FIG. 7. Further, reaction cell 73 can be transported horizontally along on rail 76 and connected to nucleic acid sample purification device 71 and nucleic acid probe purification device 72 at predetermined positions respectively on rail 76. Reference electrode 77 is immobilized onto transportation device 84 together with an end of optical fiber 78. Reference electrode 77 and optical fiber 78 can be vertically transported to the position above each vessel and horizontally transported into each vessel by means of transportation device 84. Reference electrode 77 is connected to function generator/pontentiostat 79 together with the electrode with the nucleic acid sample immobilized thereon. The voltage applied between these electrodes is controlled by computer 80. Electrochemiluminescence generated on the surface of electrode 74 with nucleic acid sample immobilized thereon is transmitted to photomultiplier 81 via optical fiber 78 for amplification and counted by photocounter 82. The results of the determination are input to computer 80 for analysis.

The gene detection using this device is conducted as follows. First, similarly to in the case of the device shown in FIG. 7, the test cells containing the nucleic acid of interest are placed in nucleic acid sample purification device 71 to prepare the test solution containing the nucleic acid sample denatured to a single-strand form. The test solution is transferred to reaction cell 73 to immobilize the nucleic acid sample on the surface of electrode 74. After completion of the immobilization of the nucleic acid sample, the test solution is discarded. Second, reaction cell 73 is transported on rail 76 to the position to be able to connect to a nucleic acid supply device, from which the probe solution containing the nucleic acid probes is led into reaction cell 73. Thereafter, the temperature of the probe solution is controlled to an appropriate value by means of temperature controller 75, and then hybridization of the nucleic acid sample immobilized on the surface of electrode 74 and the nucleic acid prove in the prove solution is conducted. At the same time, an intercalating agent which generates electrochemiluminescence is added to the probe solution. The intercalating agent can be added in the probe solution in advance. Then, reaction cell 73 is transported to a predetermined position on rail 76, and reference electrode 77 and optical fiber 78 are transported into reaction cell 73 and allowed to immerse in the probe solution. Electric voltage is applied to the position between reference electrode 77 and electrode 74 with the nucleic acid sample immobilized thereon disposed in reaction cell 73 for generating electrochemiluminescence. The electrochemiluminescence is led to photomultiplier 81 via optical fiber 78 for amplification and then counted by photocounter 82. The results of the determination are input to computer 80 for analysis. After completion of the determination, reference electrode 77 and optical fiber 78 are removed from reaction cell 73 and transferred into washing vessel 83 for washing. After determination, the nucleic acid sample immobilized on the surface of electrode 74 is removed and regenerated.

As described in detail heretofore, when the carrier with nucleic acid sample immobilized thereon is used, gene detection can be automatically carried out according to the above method using the aforementioned device. As a result, the gene can be detected more simple in a short period of time.

EXAMPLE 25

Gene Detection by use of an Electrode with a Nucleic Acid Sample Immobilized thereon a: Preparation of the electrode with a nucleic acid sample immobilized thereon.

In a gene detection model, pVM 623 was constructed by inserting a v-myc onco-gene fragment at PstI site of pUC 119 as a test sample. A synthetic oligonucleotide (20 mer) complimentary to v-myc was used as a nucleic acid probe. As an electrode, basal plane pyrolytic graphite (BPPG) was employed. The immobilization of the nucleic acid sample was performed according to the following procedures.

First, pVM 623 was digested with Hind III to obtain a linear pBM 623, which is subsequently denatured with heat at 98° C., thereby preparing a nucleic acid sample solution. Second, the BPPG electrode having polished surface was inserted in the nucleic acid sample solution. While a potential of 0.1 V was applying to the electrode, the nucleic acid was immobilized by adsorption. Immobilization of the nucleic acid sample was performed just before use. The electrode with the nucleic acid sample immobilized thereon was stored at 4° C. until use.

b: Gene detection by use of an electrode with a nucleic acid sample immobilized thereon The gene detection was carried out in the following procedures.

First, the electrode with the nucleic acid sample immobilized thereon prepared in the step a was inserted in a solution containing a nucleic acid probe and incubated at 42° C. to effect hybridization. The hybridization reaction was facilitated by intermittently applying a potential of 0.1 V (vs. SCE) to the electrode. After completion of the reaction, acridine orange was added to the solution. After the binding of acridine orange to the double-stranded nucleic acid was completed, non-specifically adsorbing substances were removed from the surface of the electrode by application of a negative charge thereto. Thereafter, the v-myc contained in the test sample was quantified by determining the oxidation-reduction current from acridine orange via BPPG electrode.

As a result, v-myc was able to detect in pg order. The entire operation was able to be automatically carried out in an hour.

Using the electrode with the nucleic acid sample immobilized thereon, the RFLP analysis can be performed. For example, in the RFLP analysis of Familial Amyloidtic Polyneuropathy (FAP), first, DNA is separated from a leukocyte of an FAP patient, cleaved with restriction enzyme BalI and fractionated by electrophoresis according to a standard method. The DNA fragments of each fraction continuously obtained in each predetermined time interval are immobilized onto the electrode. Substantially the same procedure as in the above hybridization reaction is performed using an electrode with the DNA fragment immobilized thereon. As a probe, an appropriate CDNA fragment such as a fragment of TTR gene digested with HaeII is used. As a result, the RFLP of FAP can be obtained by determining a signal level from each fractionated fragment. When the RFLP analysis is performed, it is preferable to use a tape-form electrode, for example, a tape-form BPPG electrode having a width of 5 mm.

Further, the electrode with the nucleic acid sample immobilized thereon prepared in substantially the same method as that of the section a, and a base plate with the nucleic acid sample immobilized thereon can be used in HLA typing, detection of food spoilage, and detection of contamination in pharmaceutical agents.

In the section a, the electrode with a nucleic acid probe instead of the nucleic acid sample immobilized thereon can be formed. Monitoring of the hybridization reaction by use of a gene detection sensor such as the electrode with nucleic acid probe immobilized thereon makes it possible to reduce the reaction time significantly.

EXAMPLE 26

Gene Detection by use of an Optical Fiber with a Nucleic Acid Sample Immobilized thereon a: Preparation of an optical fiber with nucleic acid sample immobilized thereon In a gene detection model, pVM 623 was constructed by inserting a v-myc onco-gene fragment at PstI site of pUC 119 as a test sample. A synthetic oligonucleotide (20 mer) complimentary to v-myc was employed as a nucleic acid probe. Immobilization of the nucleic acid sample onto the optical fiber was performed according to the following procedures.

First, pVM 623 was digested with Hind III to obtain a linear pVM 623, which was subsequently denatured with heat at 98° C., thereby preparing a nucleic acid sample solution. Second, the optical fiber was treated with a silane agent (γ-APTES) and glutaraldehyde, and then, immersed in the nucleic acid sample solution to immobilize the nucleic acid by adsorption. Immobilization of the nucleic acid sample was performed just before use. The electrode with the nucleic acid sample immobilized thereon was stored at 4° C. until use.

b: Gene detection by use of the optical fiber with a nucleic acid sample immobilized thereon The gene detection was carried out in the following procedures.

First, the optical fiber with the nucleic acid sample immobilized thereon prepared in the above section a was inserted in a solution containing a nucleic acid probe and incubated at 42° C. to effect the hybridization reaction. To this solution, acridine orange which is an intercalating agent having specificity to a double-stranded nucleic acid and a high optical activity was added. After the binding of acridine orange to the double-stranded nucleic acid was completed, v-myc contained in the test sample was quantified by determining a fluorescence generated from acridine orange via the optical fiber.

As a result, v-myc was able to detect in pg order. The entire operation was able to be automatically carried out in an hour.

EXAMPLE 27

Gene Detection by use of an Electrode with a Nucleic Acid Sample Immobilized thereon a: Preparation of the electrode with a nucleic acid sample immobilized thereon In a detection model, pVM 623 was constructed by inserting a v-myc onco-gene fragment at a PstI site of pUC 119 as a test sample. As a nucleic acid probe, use was made of synthetic oligonucleotide (20 mer) which has sequence complimentary to v-myc, to the 3' end of which, (6-aminohexyl) DATP was introduced using terminal deoxynucleotidyl transferase, and further amino acridine was bound via glutaraldehyde to an amino group of the oligonucleotide. Immobilization of the nucleic acid sample onto the BPPG electrode was performed according to the following procedures.

First, pVM 623 was digested with Hind III to obtain a linear pVM 623, which was subsequently denatured with heat at 98° C., thereby preparing a nucleic acid sample solution. Second, the BPPG electrode with a polished surface was inserted in the nucleic acid sample solution. While a potential of 0.1 V was applying to the electrode, the nucleic acid was immobilized onto the surface of the electrode by adsorption. Immobilization of the nucleic acid sample was performed just before use. The electrode with the nucleic acid sample immobilized thereon was stored at 4° C. until use.

b: Gene detection by use of the electrode with a nucleic acid sample immobilized thereon The gene detection was carried out in the following procedures.

First, the electrode with the nucleic acid sample immobilized thereon prepared in the section a was inserted in a solution containing a nucleic acid probe and incubated at 42° C. to effect the hybridization reaction. The hybridization reaction was facilitated by intermittently applying a potential of 0.1 V (vs. SCE). After completion of the reaction, the oxidation-reduction current from amino acridine being labeled on the nucleic acid prove.

As a result, v-myc was able to detect in pg order. The entire operation was able to be automatically carried out in an hour.

EXAMPLE 28

Gene Detection by use of an Optical Fiber with a Nucleic Acid Sample Immobilized thereon a: Preparation of an optical fiber with nucleic acid sample immobilized thereon In a gene detection model, pVM 623 was constructed by inserting a v-myc onco-gene fragment at a PstI site of pUC 119 was used as a test sample. As a nucleic acid probe, use was made of synthetic oligonucleotide (20 mer) which has a sequence complimentary to v-myc, to the 3' end of which, (6-aminohexyl) DATP was introduced using terminal deoxynucleotidyl transferase, and further amino acridine was bound via glutaraldehyde to an amino group of the oligonucleotide. Immobilization of the nucleic acid sample onto the optical fiber was performed according to the following procedures.

First, pVM 623 was digested with Hind III to obtain a linear pVM 623, which was subsequently denatured with heat at 98° C., thereby preparing a nucleic acid sample solution. Second, the optical fiber was treated with a silane agent (γ-APTES) and glutaraldehyde, and then immersed in the nucleic acid sample solution to immobilize a nucleic acid by adsorption. Immobilization of the nucleic acid sample was performed just before use. The electrode with nucleic acid sample immobilized thereon was stored at 4° C. until use.

b: Gene detection by use of the optical fiber with a nucleic acid sample immobilized thereon The gene detection was carried out in the following procedures.

First, the optical fiber with the nucleic acid sample immobilized thereon prepared in the section a was inserted in a solution containing a nucleic acid probe and incubated at 42° C. to effect a hybridization reaction.

After completion of the hybridization reaction, fluorescence generated from acridine orange being labeled on the nucleic acid was determined via the optical fiber.

As a result, v-myc was able to detect in pg order. The entire operation was able to be automatically carried out in an hour.

EXAMPLE 29

Screening of a Nucleic Acid Probe by use of an Electrode with a Nucleic Acid Probe Immobilized thereon.

Adult T-cell leukemia (ATL) is an infectious disease caused by retrovirus, i.e., human T-cell lymphotropic virus (HTLV). The detection of the presence of a HTLV gene makes it possible to diagnose the disease on a gene level. A nucleic acid probe candidate suitable for the gene-level diagnosis was screened from an HTLV-I gene data base using the properties as criteria that two dimensional conformation is hardly formed and a GC content is high. As a result, 10 types of probes having the sequences shown below were screened.

GTACTTTACT GACAAACCCG ACCTAC (SEQ ID NO: 1)

CCGCAGCTGC ACTAATGATT GAACTTGAGA AG (SEQ ID NO: 2)

TACTGGCCAC CTGTCCAGAG CATCAG (SEQ ID NO: 3)

GTGGTGGATT TGCCATCGGG TTTT (SEQ ID NO: 4)

CTTCACAGTC TCTACTGTGC (SEQ ID NO: 5)

CGGATACCCA GTCTACGTGT (SEQ ID NO: 6)

CCCTACAATC CCACCAGCTC AG (SEQ ID NO: 7)

CGGCAGTTCT GTGACAGGG (SEQ ID NO: 8)

GAGCCGATAA CGCGTCCACT G (SEQ ID NO: 9)

CACGCGCCCG CCCTACCTGA GGCCGCC (SEQ ID NO: 10)

a: Preparation of an electrode with a nucleic acid probe immobilized thereon 10 types of the aforementioned probes were respectively dissolved in the 1 mM Tris-HCL (pH 8.5) 1M NaCl solution. To each solution, the BPPG electrode was immersed and the nucleic acid probe was adsorbed to the electrode at 100° C. for 30 minutes. The completion of the immobilization by adsorption was identified by determining the oxidation current from a guanine residue of DNA which was obtained at cyclic voltammetry in the vicinity of 1 V.

b. Screening of a nucleic acid probe by use of an electrode with the nucleic acid probe immobilized thereon According to a standard method, DNA was extracted from the cultured cells whose infection with the HTLV has been confirmed, and cleaved with restriction enzyme SalI. On the other hand, the electrode with the nucleic acid probe immobilized thereon prepared in the section a was disposed in a reaction vessel. Temperature gradient in the range of 25° to 75° C. was provided by means of the temperature controller placed to the reaction vessel at both ends. When an electrode is disposed in the reaction vessel, 20 of the insulated electrodes having a homologous nucleic acid probe immobilized thereon were placed in the side being provided with the temperature gradient. In the side perpendicular to the temperature gradient-given side, electrodes with heterogeneous nucleic acid probe immobilized thereon were placed (see FIG. 5). Then, the sample nucleic acid sample cleaved with restriction enzyme SalI was added to the reaction vessel and hybridization was performed in 2×SSC for an hour.

After completion of the hybridization, acridine orange, which is an intercalating agent of DNA was added to the reaction solution, differential pulse voltammetry was performed with respect to each electrode. The oxidation current and a peak potential value of the signal generated from acridine orange was determined. The determination was performed under the condition of a pulse interval of 200 mV, pulse electrolysis time of 100 msec, sampling time of 200 msec, and a scanning speed of 25 mV/sec.

As a result of the determination, the signals from other probes is significantly decreased at the temperature of 60° C. or more. In contrast, in the case of the third nucleic acid probe having a sequence of 5'TACTGGCCACCTGTCCA-GAGCATCAG3' (SEQ ID NO: 11), the peak potential value of the optical signal from acridine orange showed a shift to 13 mV even at 65° C. This fact indicated that the third nucleic acid probe has been stably hybridized.

In this way, a more suitable nucleic acid probe can be obtained by applying the method of the present invention.

EXAMPLE 30

Gene Detection by use of an Electrode with the Nucleic Acid Probe Immobilized thereon To identify a point mutation at the 12th and 61st codon of amino acid of c-Ha-ras, c-Ki-ras, and N-ras oncogenes, a nucleic acid probe shown in Table 1 was synthesized and an amino group was introduced in the 5' end of the nucleic acid probe.

TABLE 1

SYNTHETIC PROBE TO RAS ONCOGENE

| Oncogene | Sequence (probe) | | Symbol | |
|---|---|---|---|---|
| c-Ha-ras/12 | GTGGGCGCCGGCGGTGTGGG | Gly (normal) | A 1 | (SE ID no:12) |
| | CGC | Arg | 2 | |
| | AGC | Ser | 3 | |
| | TGC | Cys | 4 | |
| | GAC | Asp | 5 | |
| | GCC | Ala | 6 | |
| | GTC | Val | 7 | |
| c-Ha-ras/61 | ACCGCCGGCCAGGAGGAGTA | Gln (normal) | B 1 | SEQ ID no:13) |
| | CAT | His | 2 | |
| | CAC | His | 3 | |
| | AAG | Lys | 4 | |
| | GAG | Glu | 5 | |
| | CTG | Leu | 6 | |
| | CCG | Pro | 7 | |
| | CGG | Arg | 8 | |
| c-Ki-ras/12 | GTTGGAGCTGGTGGCGTAGG | Gly (normal) | C 1 | (SEQ ID no:14) |
| | CGT | Arg | 2 | |
| | TGT | Cys | 3 | |
| | AGT | Ser | 4 | |
| | GCT | Ala | 5 | |
| | GAT | Asp | 6 | |
| | GTT | Val | 7 | |
| c-Ki-ras/61 | ACAGCAGGTCAAGAGGAGTA | Gln (normal) | D 1 | (SEQ ID no:15) |
| | AAA | Lys | 2 | |

TABLE 1-continued

SYNTHETIC PROBE TO RAS ONCOGENE

| Oncogene | Sequence (probe) | | Symbol | |
|---|---|---|---|---|
| | GAA | Glu | 3 | |
| | CGA | Arg | 4 | |
| | CCA | Pro | 5 | |
| | CTA | Leu | 6 | |
| | CAT | His | 7 | |
| | CAC | His | 8 | |
| N-ras/12 | GTTGGAGCAGGTGGTGTTGG | Gly (normal) | E 1 | (SEQ ID no:16) |
| | AGT | Ser | 2 | |
| | CGT | Arg | 3 | |
| | TGT | Cys | 4 | |
| | GCT | Ala | 5 | |
| | GAT | Asp | 6 | |
| | GTT | Val | 7 | |
| N-ras/61 | ACAGCTGGACAAGAAGAGTA | Gln (normal) | F 1 | (SEQ ID no:17) |
| | GAA | Glu | 2 | |
| | AAA | Lys | 3 | |
| | CCA | Pro | 4 | |
| | CTA | Leu | 5 | |
| | CGA | Arg | 6 | |
| | CAT | His | 7 | |
| | CAC | His | 8 | | a. Preparation of an electrode with the nucleic acid probe immobilized thereon

Figure 9:
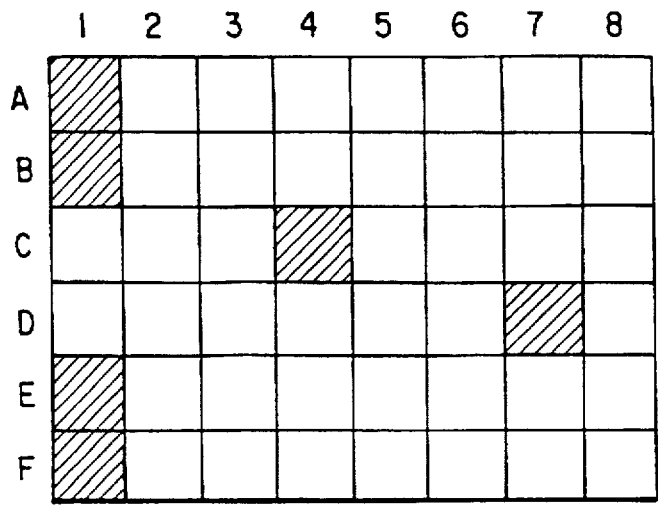
FIG. 9 shows a schematic view of the determination results in Example 30, in which a shaded box of a grid shows a positive result.

As the electrode for immobilizing the nucleic acid probe, use is made of an element made of graphite. The surface of the graphite of 5×5 cm shown in FIG. 6 was activated with an electron beam and the rear surface of which was covered with an insulating membrane. The grid having 48 boxes consisting of 6 rows and 8 lines was formed on the graphite element. To prevent contamination from other boxes, a separator was made between boxes. To each of thus formed boxes of the grid, homogenous nucleic acid probes was immobilized by use of a silane coupling agent and glutaraldehyde. The graphite base plate was connected to the insulating layer of rear surface of the boxes with the nucleic acid probes immobilized thereon by using a lead made of silver paste.

b. Gene detection by use of an electrode with the nucleic acid probe immobilized thereon Chromosomal gene (1 μg) extracted form human blood vessels was dissolved in 2×SSC. The solution containing the chromosomal gene was added to a box of the grid prepared the section a and heated to 95° C. To each box of the grid, a labeled nucleic acid probe (20 mer) having specificity to a human β globuline gene was added and hybridized each other at 42° C. The nucleic acid probe was labeled with acridine orange which covalently binds to the end of the nucleic acid probe via an amino group by use of glutaraldehyde. After completion of the hybridization reaction, the electrode was washed to remove the unreacted nucleic acid probe and electrochemical detection was performed. The result was shown in FIG. 9. The shaded box shown in FIG. 5 indicates the positive response to the hybridization. From FIG. 9, it was found that a point mutation was present in the 12th and 61st amino acid codon of Ki-ras. As mentioned above, it was shown that a plurality of examination items were able to be simultaneously carried out in one-time operation even if a test sample is present in an extremely small amount.

EXAMPLE 31

Base Sequence Determination of the Nucleic Acid Sample by use of a Base Plate with the Nucleic Acid Probe Immobilized thereon.

a. Preparation of a base plate with the nucleic acid probe immobilized thereon

Figure 10:
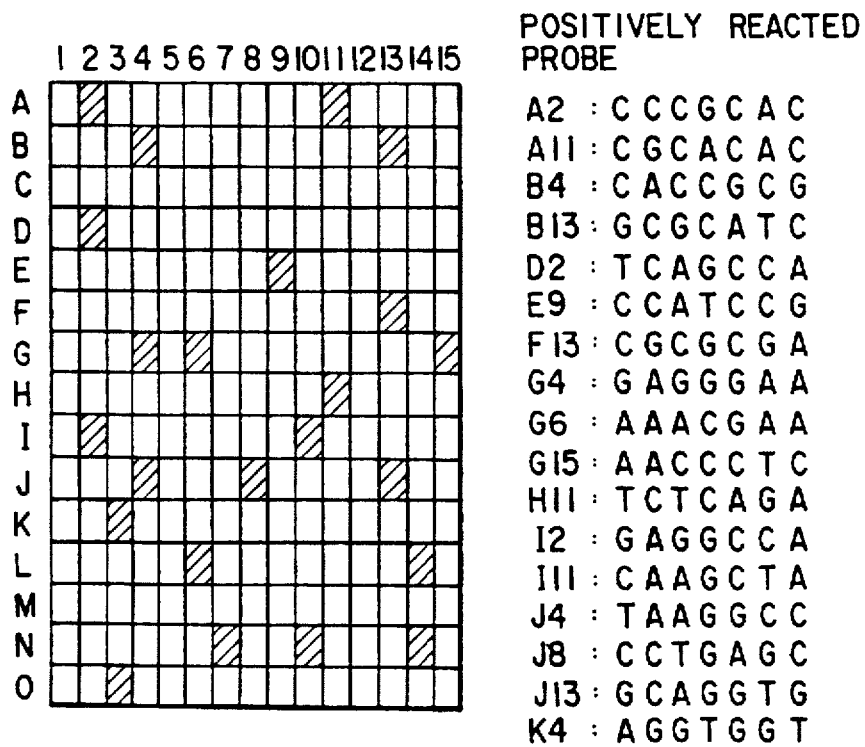
FIG. 10 shows a schematic view of the determination results in Example 31, in which a shaded box of a grid shows a positive result.

As the carrier for immobilizing the nucleic acid probe, use was made of a glass plate of 5×5 cm, on which a grid having 225 boxes consisting of 15 rows and 15 lines was formed. To each of the boxes of the grid, a heterogeneous nucleic acid probe (7 mer) having a random sequence was immobilized. A structure to be able to connect an optical fiber was given to the rear surface of each box with the nucleic acid probe immobilized thereto.

b. Base sequence determination of a nucleic acid sample by use of a base plate with the nucleic acid probe immobilized thereon a cDNA complementary to t-RNA of alanine of yeast was used as a nucleic acid sample. The cDNA was added to a box of the grid prepared the section a and heated to 95° C. After heating, to each box of the grid, a labeled nucleic acid probe (20 mer) complementary to the t-RNA of alanine was added and hybridized each other at 42° C. The nucleic acid probe was labeled with acridine orange which was allowed to bind covalently to the end of the nucleic acid probe. After completion of the hybridization reaction, the base plate was washed to remove an unreacted labeled nucleic acid probe and intensity of fluorescence generated from each box of the grid was determined. The result is shown in FIG. 10. From FIG. 10, it was found CDNA reacted to the nucleic acid probe having each sequence as follows:

CCCGCAC, CGCACAC, CACCGCG, GCGCATC, TCAGCCA, CCATCCG, CGCGCGA, GAGGGAA, AAACGAA, AACCCTC, TCTCAGA, GAGGCCA, CAAGCTA, TAAGGCC, CCTGAGC, GCAGGTG, AGGTGGT, GCACCGC, CACACCA, CGGCGCA, GGCGCAT, CATCTCA, ACCATCC

As a result of the computer analysis, it is postulated that a cDNA complementary to t-RNA of alanine of yeast has a base sequence of 3'-CCCGCACACC- GCGCATCAGC-CATCGCGCGAGGGAAACGAACCCTCTCAG AGGCCAAGCTAAGGCCTGAGCAGGTGGT-5'(SEQ ID NO: 18).

As shown above, a gene base sequence can be obtained very simply in one-time operation even if a test sample is present in an extremely small amount.

What is claimed is:

1. A gene detection method wherein a single stranded nucleic acid probe having a base sequence complementary to the gene to be detected is reacted with a gene sample denatured into a single stranded form and then said nucleic acid probe hybridized with the gene is detected to confirm the presence of the gene, comprising the steps of:

immobilizing said nucleic acid probe onto an electrode;

adding a double stranded nucleic acid recognizing substance which binds specifically to a double stranded nucleic acid and is active physicochemically to the reaction system of said nucleic acid probe and said gene sample; and detecting the presence of any double stranded nucleic acid recognizing substance bound to the double stranded nucleic acid which is formed by conjugation of said nucleic acid probe and said gene to be detected by means of electrochemical determination using said electrode.

2. The method according to claim 1, wherein a potential is applied to the electrode upon hybridization of the nucleic acid probe immobilized on the surface of the electrode and the gene sample denatured into a single stranded form.

3. The method according to claim 1, wherein said double stranded nucleic acid recognizing substance is an intercalating agent.

4. The method according to claim 3, wherein said intercalating agent is a metal complex having as a center metal capable of undergoing electrically reversible oxidation-reduction reaction and the oxidation-reduction potential of said metal is less than or is not covered by the oxidation-reduction potential of the nucleic acid.

5. The method according to claim 1, wherein said double stranded nucleic acid recognizing substance is an intercalating agent to which one or more substances generating electric signals which can be detected by said electrode directly or indirectly are bound.

6. The method according to claim 1, wherein said double stranded nucleic acid recognizing substance is a biopolymer binds specifically to a double stranded nucleic acid.

7. The method according to claim 1, wherein said nucleic acid probe is immobilized onto the electrode through an amino group introduced in said nucleic acid probe.

8. The method according to claim 1, wherein said nucleic acid probe is immobilized onto the electrode through a film.

9. The method according to claim 1, wherein said electrode is further covered with substances selected from the group consisting of nucleic acids, surfactants, fatty acids and fats.

* * * * *